US012766127B2

(12) United States Patent
Hou

(10) Patent No.: US 12,766,127 B2
(45) Date of Patent: Oct. 20, 2026

(54) ANTI-VIRAL COMPOUNDS AND METHODS FOR SCREENING SAME AND TREATING VIRAL INFECTIONS

(71) Applicant: Ming-Hung Hou, Taichung City (TW)

(72) Inventor: Ming-Hung Hou, Taichung City (TW)

( * ) Notice: Subject to any disclaimer, the term of this patent is extended or adjusted under 35 U.S.C. 154(b) by 606 days.

(21) Appl. No.: 18/014,300

(22) PCT Filed: Feb. 25, 2021

(86) PCT No.: PCT/CN2021/077938
§ 371 (c)(1),
(2) Date: Jan. 3, 2023

(87) PCT Pub. No.: WO2022/007420
PCT Pub. Date: Jan. 13, 2022

(65) Prior Publication Data

US 2023/0255935 A1 Aug. 17, 2023

Related U.S. Application Data

(60) Provisional application No. 63/048,169, filed on Jul. 5, 2020.

(51) Int. Cl.
*A61P 31/14* (2006.01)
*A61K 31/404* (2006.01)
*A61K 31/4045* (2006.01)
*A61K 31/4439* (2006.01)
*A61K 31/4709* (2006.01)
*A61P 31/20* (2006.01)

(52) U.S. Cl.
CPC ...... *A61K 31/4045* (2013.01); *A61K 31/4439* (2013.01); *A61K 31/4709* (2013.01); *A61P 31/14* (2018.01)

(58) Field of Classification Search
None
See application file for complete search history.

(56) References Cited

U.S. PATENT DOCUMENTS

2001/0007877 A1 7/2001 Burton et al.
2002/0004198 A1 1/2002 Hardwicke
2018/0362481 A1* 12/2018 Nebolsin ............ C07K 5/06104

FOREIGN PATENT DOCUMENTS

CN 102219725 A 10/2011
WO WO2009006141 A2 1/2009

OTHER PUBLICATIONS

Shan-Meng Lin, Shih-Chao Lin, Jia-Ning Hsu, Chung-ke Chang, Ching-Ming Chien, Yong-Sheng Wang, Hung-Yi Wu, U-Ser Jeng, Kylene Kehn-Hall, and Ming-Hon Hou Journal of Medicinal Chemistry 2020 63 (6), 3131-3141 (Year: 2020).*

CAS 57506-72-6 REGISTRY 1984 and CAS 1453-97-0 REGISTRY 1984 (Year: 1984).*

Hou, Ming-Hon, Hsu, Chai-Ning, Protein Science, (Dec. 2017) vol. 26, No. Suppl. 1, Sp. Iss. SI, p. 196) (Year: 2017).*

Papageorgiou et al., Structural characterization of the N-terminal part of the MERS-COV nucleocapsid by X-ray diffraction and small-angle X-ray scattering. Acta Cryst. (2016). D72, 192-202 (Year: 2016).*

Lin, Shan-Meng et al., Structure-Based Stabilization of Non-native Protein-Protein Interactions of Coronavirus Nucleocapsid Proteins in Antiviral Drug Design, Feb. 27, 2020, pp. 3131-3141, vol. 63, issue 6, Journal of Medical Chemistry.

Hogan, Iain T D., The chemical regulation of carcinogenesis, 1985, 14 pages, for the degree of Doctor of Philosophy of the Univesity of Bath.

Shaw, E., The Synthesis of Tryptamines Related to Serotonin, Feb. 28, 1955, pp. 4319-4324, vol. 77, issue 16, Journal of the American Chemical Society.

Registry of STN, CAS 1020245-18-4, ACS, Entered STN: Jan. 24, 2014, 1 page.

Alemany, A. et al., Inhibiteur d'enzymes. XV.—Préparation de (propargylamino méthyl)-3 indoles, 1975, pp. 1223-1227 Bulletin de la Société Chimique de France, No. 5-6.

Friderichs, E et al., Über Serotoninderivate mit cyclisierter Seitenkette, 1. Mitt. Darstellung derisomeren 3-(Pyridiylmethyl)-und 3-(Piperidylmethyl)-5-hydroxyindole, Jul. 8, 1975, pp. 209-217, Arch. Pharmaz., vol. 308, issue 3.

Gim, H. J. et al., Identification of a Novel PPAR-γ Agonist Through a Scaffold Tuning Approach, Oct. 4, 2018, 18 pages, International Journal of Molecular Sciences.

* cited by examiner

*Primary Examiner* — Kortney L. Klinkel
*Assistant Examiner* — Alison Azar Hastings
(74) *Attorney, Agent, or Firm* — MUNCY, GEISSLER, OLDS & LOWE, P.C.

(57) ABSTRACT

Provided is a compound of formula (I), where $R_1$ to $R_4$ are as defined herein, and a method for treating a viral infection in a subject in need thereof by administering with the compound. Also provided is a method for screening a compound capable of inhibiting activities of a coronavirus in a host cell, including identifying a compound that modulates a non-native protein-protein interaction in coronaviral nucleocapsid (N) proteins.

(I)

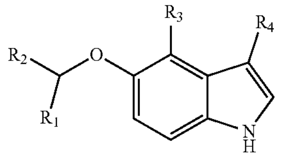

7 Claims, 27 Drawing Sheets

Specification includes a Sequence Listing.

ANTI-VIRAL COMPOUNDS AND METHODS FOR SCREENING SAME AND TREATING VIRAL INFECTIONS

REFERENCE TO AN ELECTRONIC SEQUENCE LISTING

The content of the electronic sequence listing (2023-01-03_Sequence_Listing.txt; Size: 9287 bytes; and Date of Creation: Jan. 3, 2023) is herein incorporated by reference in its entirety.

BACKGROUND

1. Technical Field

The present disclosure relates to the field of antiviral therapy and, in particular, to compounds for treating viral infections and methods for screening antiviral compounds capable of inhibiting viral activities.

2. Description of Related Art

Epidemics caused by coronaviruses (CoVs), e.g., severe acute respiratory syndrome (SARS) in 2003, Middle East respiratory syndrome (MERS) in 2012, and coronavirus disease 2019 (COVID-19) in 2019, have triggered a global public health emergency. As the diseases are spreading worldwide, there are currently no FDA-approved antiviral drugs or vaccines available for controlling the outbreaks.

Thus, there exists an unmet need to identify competent compounds that have potential to effectively treat coronavirus infections.

SUMMARY

In view of the foregoing, the present disclosure provides a compound that is capable of modulating a non-native protein-protein interaction in coronavirus N proteins and thereby treating a viral infection.

In at least one embodiment of the present disclosure, the compound is represented by formula (I) below:

(I)

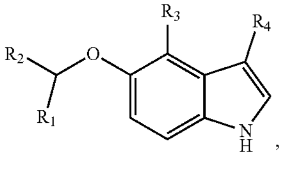

wherein:

each of $R_1$ and $R_2$, independently, is H or a substituted or unsubstituted moiety selected from the group consisting of alkyl, alkenyl, alkynyl, haloalkyl, aryl, alkaryl, heteroaryl, heteroalkaryl, alkoxy, acyloxy, hydroxyl, cycloalkyl, and heterocyclyl;

$R_3$ is H or a substituted or unsubstituted moiety selected from the group consisting of alkoxy, acyloxy, silyloxy, hydroxyl, thio, thioether, thiophenyl, mercapto, alkylmercapto, sulfo, amino, alkylamino, acylamino, and sulfamido; and $R_4$ is H or a substituted or unsubstituted moiety selected from the group consisting of alkyl, aryl, aralkyl, heteroaralkyl, cycloalkyl, heterocyclyl, alkylamino, amino, imino, aminoalkyl, aminocarbonyl, amido, imidoyl, acyl, and carbamoyl, with the proviso that $R_1$ and $R_2$ are not H at the same time, and $R_3$ and $R_4$ are not H at the same time.

In at least one embodiment of the present disclosure, the substituted moiety in the compound of formula (I) is optionally substituted by one or more substituents selected from the group consisting of alkyl, alkenyl, alkynyl, hydroxyalkyl, fluoroalkyl, chloroalkyl, bromoalkyl, iodoalkyl, perfluoroalkyl, aryl, heteroaryl, cycloalkyl, cycloalkenyl, carboxyl, aralkyl, aralkenyl, aralkynyl, heteroaralkyl, heteroaralkenyl, heteroaralkynyl, heterocyclyl, acyl, aminocarbonyl, aminoalkyl, amino, hydroxyl, alkoxy, aryloxy, silyloxy, amido, imidoyl, carbamoyl, halo, phosphate group, thio, thioether, sulfo, and sulfamido. In some embodiments, the substituted moiety consists of the moiety and at least one substituent as mentioned above.

In at least one embodiment of the present disclosure, in the compound of formula (I), each of $R_1$ and $R_2$, independently, is H or a substituted or unsubstituted moiety selected from the group consisting of alkyl, haloalkyl, aryl, heteroaryl, alkoxy, acyloxy, and hydroxyl; $R_3$ is H or a substituted or unsubstituted moiety selected from the group consisting of alkoxy and acyloxy; and $R_4$ is H or a substituted or unsubstituted moiety selected from the group consisting of alkyl, aryl, aralkyl, heteroaralkyl, and aminoalkyl, with the proviso that $R_1$ and $R_2$ are not H at the same time, and $R_3$ and $R_4$ are not H at the same time. In some embodiments, $R_4$ is selected from the group consisting of benzyl, pyridinemethyl, $-NCH_3C_2H_5$, $-NHCH(CH_3)_2$, $-NCH_3CH_2OH$, $-CH_2N(CH_3)_2$, $-CH_2NCH_3C_2H_5$, $-CH_2NHCH(CH_3)_2$, $-CH_2NCH_3CH_2OH$, and $-(C_2H_2)_2CH(CH_3)OCH_2CH_3$.

In at least one embodiment of the present disclosure, the compound is represented by formula (II) below:

(II)

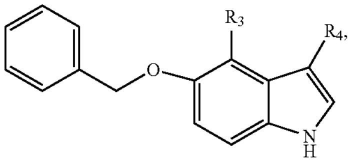

wherein $R_3$ is H or a substituted alkoxy, and $R_4$ is H or a substituted moiety selected from the group consisting of alkyl, aralkyl, heteroaralkyl, and aminoalkyl, with the proviso that $R_3$ and $R_4$ are not H at the same time.

In at least one embodiment of the present disclosure, the viral infection is caused by a coronavirus. In some embodiments, the coronavirus is a β-coronavirus. In some embodiments, the coronavirus is SARS-CoV, MERS-CoV, SARS-CoV2 (i.e., the virus of COVID-19), mouse hepatitis virus (MHV), or porcine epidemic diarrhea virus (PEDV).

In at least one embodiment of the present disclosure, a method for treating a viral infection in a subject in need thereof is provided. The method comprises administering to the subject an effective amount of the above-mentioned compound.

In at least one embodiment of the present disclosure, the compound is administered orally, intraperitoneally, intravenously, intradermally, intramuscularly, subcutaneously, or transdermally.

In at least one embodiment of the present disclosure, a method for screening a compound capable of inhibiting replication of a coronavirus in a host cell is further provided. The method comprises identifying a compound that modulates a non-native protein-protein interaction (PPI) in coronaviral N proteins.

In at least one embodiment of the present disclosure, the compound stabilizes the non-native PPI. In some embodiments, the non-native PPI is a dimerization of the N-terminal domains of the N proteins (N-NTDs). In some embodiments, the compound inhibits the replication of coronavirus by stabilizing the non-native PPI and inducing abnormal N protein oligomerization.

In at least one embodiment of the present disclosure, the N-NTDs bind to each other through a dimeric interface thereof to form the dimerization. In some embodiments, the compound stabilizes the binding generated in the dimeric interface by forming a hydrophobic contact with the dimeric interface.

In at least one embodiment of the present disclosure, the dimeric interface of the N-NTDs comprises a hydrophobic pocket. In some embodiments, the compound and the hydrophobic pocket form the hydrophobic contact. In some embodiments, the hydrophobic contact is formed between the compound and at least one of V41, W43, and F135 in the hydrophobic pocket. In some embodiments, the hydrophobic contact is formed between the compound and at least one of V41, W43, N66, N68, N73 and F135 in the hydrophobic pocket. In some embodiments, the hydrophobic contact is formed between the compound and at least one of V41, W43, N66, N68, S69, T70, N73, G104, T105, G106, A109, F135 and T137 in the hydrophobic pocket.

In at least one embodiment of the present disclosure, the identification is detecting a hydrophobic contact formed between the compound and a hydrophobic pocket of the dimeric interface of the N-NTDs.

In the present disclosure, the compound provided in the present disclosure as an antivirus agent may inhibit virus replication and reduce the amount of viruses in a host cell. Hence, the method of the present disclosure is effective in treating a viral infection. The present disclosure also provides an alternative strategy for antivirus drug discovery, which is useful in accelerating the development of anti-coronavirus drugs, so as to control the outbreak of coronavirus.

BRIEF DESCRIPTION OF THE DRAWINGS

The present disclosure can be more fully understood by reading the following descriptions of the embodiments, with reference made to the accompanying drawings.

FIG. 1A is a schematic diagram showing an overall structure of the MERS-CoV N-NTD dimer containing monomers 1 and 2, and the residues involved in dimerization shown as sticks; and polar contacts are indicated with dashed lines. FIG. 1B shows close-up of the interacting region of vector-fusion residues (upper panel) and 2D diagrams of the interaction between the hydrophobic pocket and the vector-fusion residues (lower panel), wherein the surface is in grey level according to the hydrophobicity level at the protein surface, and the hydrophobic contacts are indicated with dashed lines. FIG. 1C is a sequence alignment of various CoV N proteins in the N-terminal region, wherein the sequence of MERS N protein is used as a reference for the alignment, and thus the indicated numbers are referred to the positions of amino acid residues on the sequence of MERS N protein. Letters indicate strictly conserved residues and conservative substitution sites; and hydrophobic regions involved in unusual dimerization are indicated by black triangles. The sequences of N proteins of MERS, human coronavirus (HCoV), MHV, SARS and bat coronavirus (BtCoV) are partly represented by SEQ ID NOs. 1 to 5 provided in the accompanying Sequence Listing, which are derived from NCBI Accession NOs. ATG84895.1, AMK59681.1, ADI59793.1, ACB69868.1, and AVP25404.1, respectively. FIG. 1D shows a result of cross-linking analysis of wild-type (WT) MERS-CoV N-NTD and various MERS-CoV N-NTD mutants, wherein black arrows indicated the expected positions of the protein dimer (D) and monomer (M). FIG. 1E shows the superimposed structure achieved by aligning the MERS-CoV N-NTD containing vector-fusion residues to that containing native residues (PDB: 4ud1; shown in cyan), wherein the black box highlights the flexible region, and the residues from the vector and corresponding residues from the native MERS are shown as sticks and labeled with V and M in brackets, respectively. S42 indicates the starting point of the flexible area.

FIG. 3A is a normalized result from GNOM showing pairwise distance distribution P(r) and maximum distance ($D_{max}$); $R_g$: radius of gyration. FIGS. 3B and 3C are scattering profiles of the N protein (NP, FIG. 3B) and the NP-PSX-01 complex (NP:PSX-01, FIG. 3C) and normalization fitting with GNOM (dashed lines). FIGS. 3D and 3E are representative models of the N protein (FIG. 3D) and the NP-PSX-01 complex (FIG. 3E) generated by CRYSOL simulations of the small-angle X-ray scattering (SAXS) data. Only a carbons are shown. FIGS. 3F and 3G show the results of conformation (FIG. 3F) and stability analyses (FIG. 3G) based on fluorescence (FL) spectra of the MERS-CoV N protein (1 μM) incubated with PSX-01 (10 μM) for 1 h in a buffer containing 50 mM Tris-HCl and 150 mM NaCl (pH 8.3). FIG. 3H is a schematic diagram of the PSX-01 inhibition mechanism. Left panel: in the absence of RNA, N proteins organized as a dimeric building block contributed by N-CTD dimerization; middle panel: PSX-01 promoted the dimerization of N-NTDs from different building blocks, by which the distance between CTD cuboids was shortened and N protein aggregation occurred; right panel: octameric conformation of building blocks buried in the RNA-binding surface of N-CTDs, which hindered the formation of filamentous ribonucleocapsids.

FIGS. 4A and 4B show that viral titers (FIG. 4A) and RNA (FIG. 4B) of MERS-CoV measured by plaque assay and RT-qPCR, respectively, decrease after PSX-01 treatment for 48 h. Relative RNA levels were determined by comparing MERS alone at each time point. GAPDH RNA was used as the internal control. All values are presented as mean±SE (standard error of mean). One-way Anova was used for statistics (*$p<0.05$, $p<0.01$, *$p<0.001$). FIG. 4C shows that MERS-CoV nucleocapsid protein decreases after 48 h PSX- 01 treatment. Nucleocapsid protein expressions were examined under a confocal microscope at ×680. Nuclei were stained with DAPI.

DETAILED DESCRIPTION OF THE EMBODIMENTS

Figure 1A:
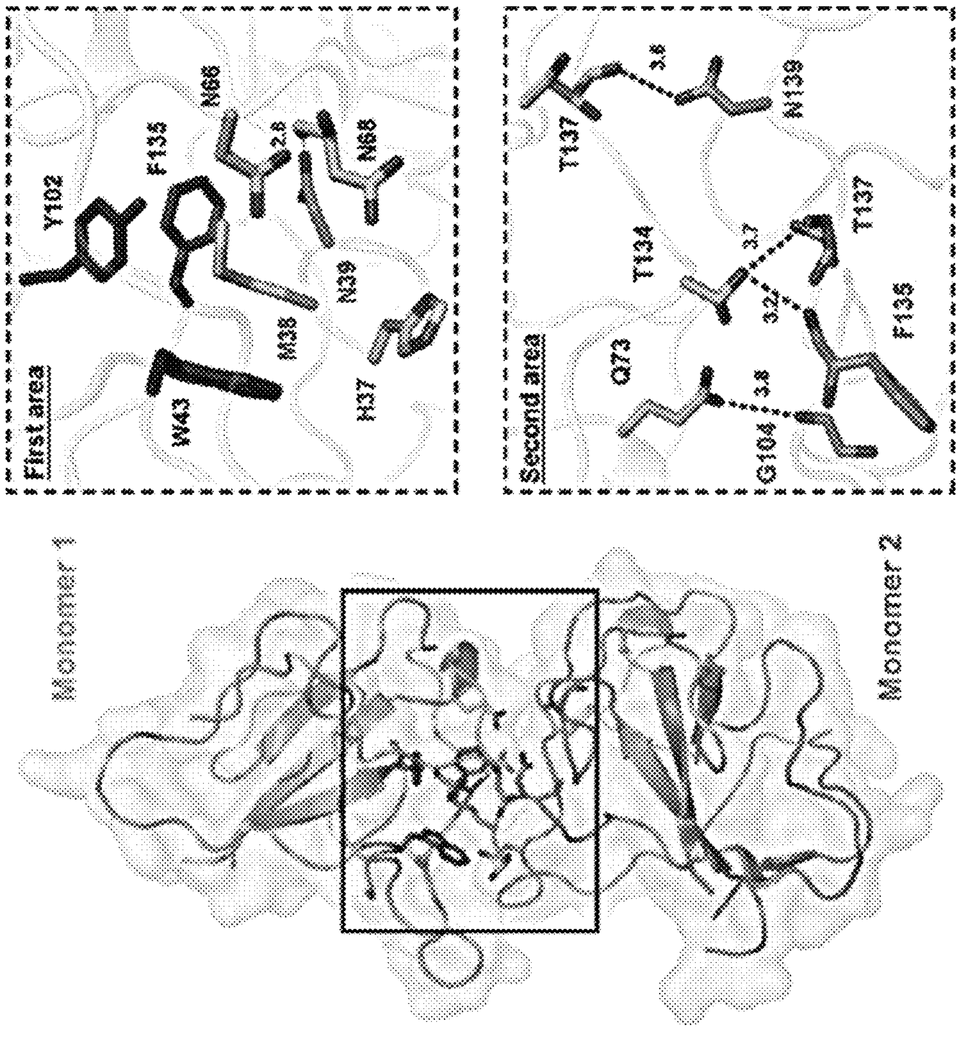
FIGS. 1A to 1E show the structure and sequence of MERS-CoV N-NTD.

The following examples are used for illustrating the present disclosure. A person skilled in the art can easily conceive the other advantages and effects of the present disclosure, based on the disclosure of the specification. The present disclosure can also be implemented or applied as described in different examples. It is possible to modify or alter the following examples for carrying out this disclosure without contravening its scope, for different aspects and applications.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

As used herein, the term "comprising" or "comprises" is used in reference to compositions, methods, and respective component(s) thereof, that are included in the present disclosure, yet open to the inclusion of unspecified elements or steps, whether essential or not.

The present disclosure is directed to a method for treating a viral infection in a subject in need thereof and a method for screening and identifying a compound capable of inhibiting viral activities, such as replication, in a host cell.

In at least one embodiment, the viral infection treated by the method of the present disclosure may be caused by coronavirus (CoV).

The structural proteins of CoVs including nucleocapsid (N), small envelope (E), matrix (M) and trimeric spike (S) glycoproteins, which are essential for virion assembly and function to complete the viral life cycle during infections. Among the structural proteins of CoVs, N proteins are a major structural component with relative conserved evolution, and share the same modular organization which consists of intrinsically disordered regions (IDRs): an N-arm, a C-arm, and two structural domains including an N-terminal RNA-binding domain (NTD) and a C-terminal dimerization domain (CTD).

All CoV N-NTD structures are folded in a monomeric conformation. In contrast, the CoV N-CTDs are always dimeric and are responsible for N protein oligomerization via protein-protein interactions. Dimeric N protein functions as a building block by binding to the viral RNA, forming a ribonucleoprotein (RNP) complex, which is a primary part of viral self-assembly for subsequent viral replication and translation. Furthermore, the N protein also involves in regulating host cell cycle and viral pathogenesis, ultimately facilitating virus production.

Since the protein-protein interaction (PPI) between dimeric N proteins plays a role in viral replication, structure-based stabilization of PPI is a promising strategy for drug discovery. Stabilizing PPIs with small molecules may be allosteric or orthosteric (also called direct). This process alters the oligomerization equilibrium of the protein and enables small molecules to modulate physiological functions of the protein.

In at least one embodiment, the compound provided in the present disclosure may inhibit replication of coronavirus by modulating a non-native PPI in coronaviral N proteins, thereby inducing abnormal aggregation of coronaviral N proteins and reducing the amount of viruses in the host. Accordingly, the compound identified by the method of the present disclosure may have antiviral activity and be useful for treating viral infections.

In at least one embodiment, the non-native protein-protein interaction is a dimerization of N-NTDs, which may result in abnormal aggregation of N proteins. In some embodiments, the compound of the present disclosure may stabilize the dimerization of N-NTDs, thereby inhibiting viral replication.

In at least one embodiment, the compound identified by the present disclosure may mediate dimerization of non-native CoV N-NTDs and induce aggregation of abnormal N proteins by influencing the oligomeric behavior of N-CTDs and eventually halting its function in RNP formation.

For β-coronaviruses such as MERS-CoV, the amino acids comprising the non-native interaction interface on N-NTDs are relatively conserved. This conservation may facilitate developing compounds with broad-spectrum activity against a target pathogen family, including SARS-CoV2. Therefore, the present disclosure provides a solution for development of a new therapeutic approach based on stabilizing a non-native protein interaction interface. It may lead to discovery and development of alternative treatments for various infectious diseases.

In at least one embodiment, the compound of the present disclosure may be represented by formula (I) below:

(I)

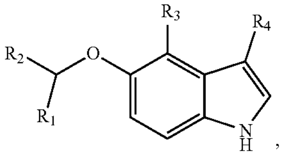

wherein:

each of $R_1$ and $R_2$, independently, is H or a substituted or unsubstituted moiety selected from the group consisting of alkyl, alkenyl, alkynyl, haloalkyl, aryl, alkaryl, heteroaryl, heteroalkaryl, alkoxy, acyloxy, hydroxyl, cycloalkyl, and heterocyclyl;

$R_3$ is H or a substituted or unsubstituted moiety selected from the group consisting of alkoxy, acyloxy, silyloxy, hydroxyl, thio, thioether, thiophenyl, mercapto, alkylmercapto, sulfo, amino, alkylamino, acylamino, and sulfamido; and $R_4$ is H or a substituted or unsubstituted moiety selected from the group consisting of alkyl, aryl, aralkyl, heteroaralkyl, cycloalkyl, heterocyclyl, alkylamino, amino, imino, aminoalkyl, aminocarbonyl, amido, imidoyl, acyl, and carbamoyl, with the proviso that $R_1$ and $R_2$ are not H at the same time, and $R_3$ and $R_4$ are not H at the same time.

The term "alkyl" as used herein refers to unsaturated hydrocarbon groups in a straight, branched, or cyclic configuration (also referred to as "cycloalkyl" below). Exemplary alkyl groups include lower alkyl groups (e.g., those having twelve or less carbon atoms), such as methyl, ethyl, propyl, isopropyl, butyl, sec-butyl, tertiary butyl, pentyl, isopentyl, hexyl, and isohexyl.

The term "alkenyl" as used herein refers to an alkyl group as defined above and having at least one double bond. Exemplary alkenyl groups include straight, branched, or cyclic alkenyl groups having two to twelve carbon atoms (e.g., ethenyl, propenyl, butenyl, and pentenyl).

Similarly, the term "alkynyl" as used herein refers to an alkyl or alkenyl group as defined above and having at least one triple bond. Exemplary alkynyl groups include straight, branched, or cyclic alkynes having two to twelve carbon atoms (e.g., ethynyl, propynyl, butynyl, and pentynyl).

The term "cycloalkyl" as used herein refers to a cyclic alkane (in which a chain of carbon atoms of a hydrocarbon forms a ring) including three to eight carbon atoms. Exemplary cycloalkanes include cyclopropyl, cyclobutyl, cyclopentyl, cyclohexyl, cycloheptyl, and cyclooctyl. In the present disclosure, the cycloalkyl groups may also include a double or triple bond (and may therefore also be termed as cycloalkenyl or cycloalkynyl).

The term "aryl" as used herein refers to an aromatic carbon atom-containing ring, which may further include one or more non-carbon atoms (also referred to as "heteroaryl"). Exemplary aryl groups include cycloalkenyls (e.g., phenyl and naphthyl) and pyridyl. Exemplary heteroaryl groups include 5- and 6-membered rings with nitrogen, sulfur, phosphorus, or oxygen as a non-carbon atom (e.g., imidazole, pyrrole, triazole, dihydropyrimidine, indole, pyridine, thiazole, and tetrazole).

As also used herein, the term "heterocyclyl" refers to any compound in which a plurality of atoms forms a 3- to 14-membered ring via a plurality of covalent bonds, wherein the ring includes at least one atom other than a carbon atom (e.g., nitrogen, oxygen, and sulfur). An example of a heterocyclyl group is a cycloalkyl group (e.g., cyclopentyl or cyclohexyl) with one or more (e.g., 1, 2 or 3) ring atoms being replaced by heteroatoms selected from N, S, or O. Exemplary heterocyclyl groups containing one heteroatom include pyrrolidine, tetrahydrofuran, dihydrofuranyl and piperidine, and exemplary heterocyclyl groups containing two heteroatoms include morpholine and piperazine. A further example of a heterocyclyl group is a cycloalkenyl group (e.g., a cyclohexenyl group) with one or more (e.g. 1, 2 or 3) ring atoms being replaced by heteroatoms selected from N, S and O.

The term "alkoxy" as used herein refers to straight or branched chain alkoxides, wherein the hydrocarbon portion may have any number of carbon atoms (and may further include a double or triple bond), such as alkyl, aryl, arylalkyl, and cycloalkyl. For example, suitable alkoxy groups include methoxy, ethoxy, and isopropoxy. Similarly, the term "alkylmercapto" denotes the group "—SR," where R may be defined as above, e.g., alkyl, aryl, arylalkyl, and cycloalkyl. Furthermore, the term "aryloxy" denotes the group "—OAr," where Ar is aryl or heteroaryl.

It should also be recognized that all, or almost all of the above-defined groups, may be substituted with one or more substituents, which may in turn be substituted as well. For example, the phrase "substituted alkyl" refers to alkyl as just described that includes one or more substituents of alkyl, alkenyl, alkynyl, hydroxyalkyl, fluoroalkyl, chloroalkyl, bromoalkyl, iodoalkyl, perfluoroalkyl, aryl, heteroaryl, cycloalkyl, cycloalkenyl, carboxyl, aralkyl, aralkenyl, aralkynyl, heteroaralkyl, heteroaralkenyl, heteroaralkynyl, heterocyclyl, acyl, aminocarbonyl, aminoalkyl, amino, hydroxyl, alkoxy, aryloxy, silyloxy, amido, imidoyl, carbamoyl, halo, thio, thioether, sulfo, and sulfamido.

In at least one embodiment, the present disclosure provides a method for treating a viral infection in a subject in need thereof, comprising administering to the subject an effective amount of the above-mentioned compound.

As used herein, the term "treating" or "treatment" refers to obtaining a desired pharmacologic and/or physiologic effect, e.g., inhibition of viral replication. The effect may be prophylactic in terms of completely or partially preventing a disease or symptom thereof, or may be therapeutic in terms of completely or partially curing, alleviating, relieving, remedying, or ameliorating a disease or an adverse effect attributable to the disease or symptom.

As used herein, the terms "patient" and "subject" are used interchangeably. The term "subject" means a human or animal. Examples of the subject include, but are not limited to, human, monkey, mice, rat, woodchuck, ferret, rabbit, hamster, cow, horse, pig, deer, dog, cat, fox, wolf, chicken, emu, ostrich, and fish. In some embodiments of the present disclosure, the subject is a mammalian, e.g., a primate such as a human.

As used herein, the phrase "an effective amount" refers to the amount of an active agent (e.g., an antivirus agent) that is required to confer a desired therapeutic effect on the treated subject (e.g., reducing the amount of viruses in a host). Effective doses will vary, as recognized by those skilled in the art, depending on routes of administration, excipient usage, the possibility of co-usage with other therapeutic treatment, and the condition to be treated.

As used herein, the term "administering" or "administration" refers to the placement of an active agent (e.g., an antivirus agent) into a subject by a method or route which results in at least partial localization of the active agent at a desired site to produce the desired effect. The active agent described herein may be administered by any appropriate route known in the art including, but not limited to, oral or parenteral routes, including intraperitoneal, intravenous, intradermal, intramuscular, subcutaneous, or transdermal routes.

In at least one embodiment, the compound may be formulated into a pharmaceutical composition for administration.

In at least one embodiment, the present disclosure provides a pharmaceutical composition for treating a viral infection. The pharmaceutical composition comprises the above compound as an antivirus agent in an effective amount and a pharmaceutically acceptable carrier thereof.

In at least one embodiment, the pharmaceutically acceptable carrier may be diluents, disintegrants, binders, lubricants, glidants, surfactants, or any combination thereof.

In at least one embodiment, the pharmaceutical composition is a sterile injectable composition, which may be a solution or suspension in a non-toxic parenterally acceptable diluent or solvent. Among the acceptable vehicles and solvents that may be employed are mannitol, 1,3-butanediol, water, Ringer's solution, and isotonic sodium chloride solution. In addition, fixed oils are conventionally employed as a solvent or suspending medium (e.g., synthetic mono- or di-glycerides). Fatty acids, such as oleic acid and its glyceride derivatives, are useful in the preparation of injectables, as naturally pharmaceutically acceptable oils, such as olive oil and castor oil, in their polyoxyethylated versions. These oil solutions or suspensions may also contain a long chain alcohol diluent or dispersant, carboxymethyl cellulose, or similar dispersing agents. Other commonly used surfactants such as Tweens and Spans or other similar emulsifying agents or bioavailability enhancers which are commonly used in the manufacture of pharmaceutically acceptable solid, liquid, or other dosage forms may also be used for the purpose of formulation.

The carrier in the pharmaceutical composition is "acceptable" in the sense that it is compatible with the active agent of the composition (e.g., capable of stabilizing the active agent) and not deleterious to the subject to be treated. One or more solubilizing agents may be utilized as pharmaceutical excipients for delivery of an active compound. Examples of other carriers include colloidal silicon oxide, magnesium stearate, cellulose, and sodium lauryl sulfate.

Many examples have been used to illustrate the present disclosure. The examples below should not be taken as a limit to the scope of the present disclosure.

EXAMPLES

Materials and Methods

The materials and methods used in the following Examples 1-7 were described in detail below. The materials used in the present disclosure but unannotated herein are commercially available.

(1) Chemicals

The compounds P1 (i.e., benzyl 2-(hydroxymethyl)-1-indolinecarboxylate), P2 (i.e., etodolac), and PSX-01 (i.e., 5-benzyloxygramine) were purchased from Maybridge Chemical Company, TCI Chemicals, and Sigma-Aldrich Corporation, respectively. The reagents used in this disclosure were purchased from Sigma Chemical Co. (St. Louis, MO). The purity of all compounds is higher than 95% and was used without further purification.

The compounds P3-1 to P3-7 were synthesized by the general processes known in the field of chemical synthesis and briefly described as below.

(1-1) Compound P3-1: 8-(((5-(benzyloxy)-1H-indol-4-yl)oxy)methyl)quinolone

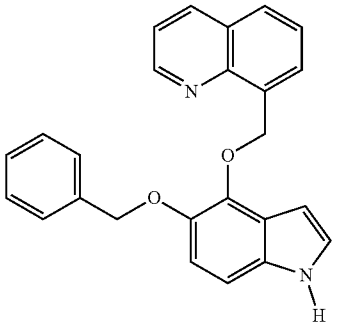 [SMILES: c1ccc(COc2ccc3[nH]ccc3c2OCc2cccc3cccnc23)cc1]

Oxy-methylquinoline and benzyloxy were added at the 4 and 5 positions of indole.

(1-2) Compound P3-2: 3-benzyl-5-(benzyloxy)-1H-indole

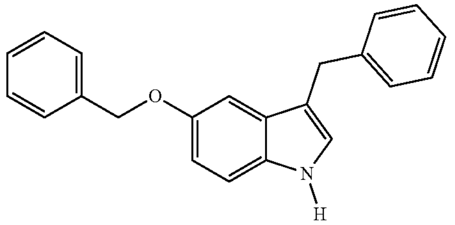 [SMILES: c1ccc(COc2ccc3[nH]cc(Cc4ccccc4)c3c2)cc1]

Benzyl and benzyloxy were added at the 3 and 5 positions of indole.

(1-3) Compound P3-3: 5-(benzyloxy)-3-(3-ethoxybutyl)-1H-indole

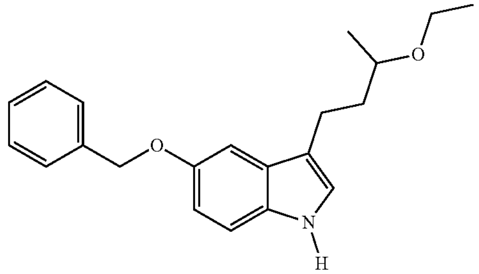 [SMILES: CCOC(C)CCc1c[nH]c2ccc(OCc3ccccc3)cc12]

3-Ethoxybutyl and benzyloxy were added at the 3 and 5 positions of indole.

(1-4) Compound P3-4: N-((5-(benzyloxy)-1H-indol-3-yl)methyl)-N-methylethanamine

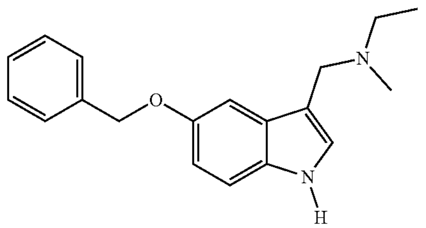 [SMILES: CCN(C)Cc1c[nH]c2ccc(OCc3ccccc3)cc12]

Methyl-N-methylethanamine and benzyloxy were added at the 3 and 5 positions of indole.

(1-5) Compound P3-5: 5-(benzyloxy)-3-(pyridin-2-ylmethyl)-1H-indole

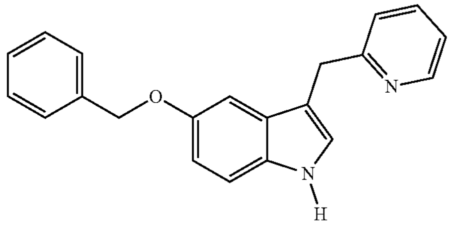 [SMILES: c1ccc(COc2ccc3[nH]cc(Cc4ccccn4)c3c2)cc1]

Pyridin-2-ylmethyl and benzyloxy were added at the 3 and 5 positions of indole.

(1-6) Compound P3-6: N-((5-(benzyloxy)-1H-indol-3-yl)methyl)propan-2-amine

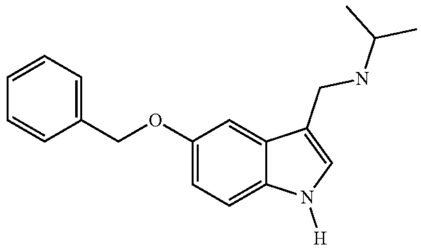 [SMILES: CC(C)NCc1c[nH]c2ccc(OCc3ccccc3)cc12]

Methyl propan-2-amine and benzyloxy were added at the 3 and 5 positions of indole.

(1-7) Compound P3-7: (((5-(benzyloxy)-1H-indol-3-yl)methyl)(methyl)amino)methanol

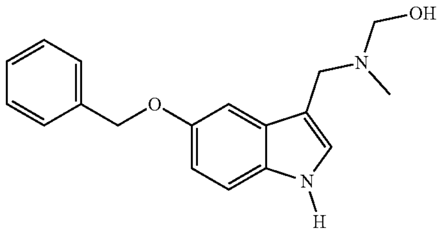 [SMILES: CN(CO)Cc1c[nH]c2ccc(OCc3ccccc3)cc12]

Methyl-(methyl)amino-methanol and benzyloxy were added at the 3 and 5 positions of indole.

(2) Cloning, Protein Expression, and Purification

The MERS-CoV N proteins were prepared according to previously described methods [1]. In brief, the cDNA fragments of MERS-CoV N proteins were cloned into a pET-28a expression vector (Merck, Darmstadt, Germany) containing a histidine tag-encoding sequence. Vectors encoding the single mutants N39A, N39G, and W43A were generated using the QuikChange site-directed mutagenesis protocol with the primers listed in Table 1 below.

TABLE 1

Primers used for mutagenesis in this disclosure

| Primer* | | Sequence | SEQ ID NO. |
|---|---|---|---|
| N39A | F | 5'-CCGCGCGGCAGCCATATGGCGACCGTGAGCTGGTATACC-3' | 6 |
| | R | 5'-GGTATACCAGCTCACGGTCGCCATATGGCTGCCGCGCGG-3' | 7 |
| N39G | F | 5'-CCGCGCGGCAGCCATATGGGCACCGTGAGCTGGTATACC-3' | 8 |
| | R | 5'-GGTATACCAGCTCACGGTGCCCATATGGCTGCCGCGCGG-3' | 9 |
| W43A | F | 5'-CATATGAACACCGTGAGCGCGTATACCGGCCTGACCCAG-3' | 10 |
| | R | 5'-CTGGGTCAGGCCGGTATACGCGCTCACGGTGTTCATATG-3' | 11 |

*F: Forward; R: Reverse

The vectors were transformed into *Escherichia coli* BL21 (DE3) pLysS cells. The cells were grown to an optical density range of 0.6 to 0.8 at 600 nm at 37° C., and protein expression was induced with 1.0 mM isopropyl β-D-1-thiogalactopyranoside (IPTG), followed by incubation at 10° C. for 24 hours (h). The cells were harvested by centrifugation (6,000 g, 12 min, 4° C.) and resuspended in lysis buffer (150 mM NaCl, 50 mM Tris-HCl, 15 mM imidazole, and 1 mM phenylmethylsulfonyl fluoride (PMSF); pH 7.5). The cells were lysed by sonication and centrifuged (10,000 g, 40 min, 4° C.) to remove debris. The supernatant was purified by injection into a Ni-NTA column (Merck, Darmstadt, Germany) and eluted with a buffer containing imidazole at a gradient range of 15 to 300 mM. Pure protein fractions were collected, dialyzed with a low-salt buffer, concentrated, and quantified by the Bradford method (BioShop Canada Inc., Burlington, ON, Canada).

(3) Crystallization and Data Collection

MERS-CoV N-NTD crystals were grown as previously described [1]. In brief, MERS-CoV N-NTD was crystallized at room temperature (around 25° C.) by the sitting-drop vapor-diffusion method. A protein solution (2 μL; 10 mg/mL) was mixed with an equal volume of a crystallization solution consisting of 75 mM ammonium sulfate, 2 mM NaBr, and 29% PEG 3350 (Sigma-Aldrich Corp., St. Louis, MO) and equilibrated against a 300 μL solution. MERS-CoV N-NTD:PSX-01 co-crystals were obtained using a crystallization solution containing 2 mM PSX-01. MERS-CoV N-NTD crystals in complex with P1 were obtained by soaking native MERS-CoV N-NTD crystals for 90 sec at room temperature in a crystallization solution containing 2 mM P1. Diffraction datasets for MERS-CoV N-NTD alone and in complex with P1 were collected at beamline 13B1 of the Taiwan Light Source (TLS) of the National Synchrotron Radiation Research Center (NSRRC; Hsinchu City, Taiwan). Diffraction of the MERS-CoV N-NTD:PSX-01 complex was performed at the beamline SP44XU of SPring-8 (Hyogo, Japan).

(4) Structural Determination and Refinement

Diffraction data were processed and scaled with HKL-2000 software. The structures were solved by molecular replacement (MR) in Phenix [2] using HCoV-OC43 N-NTD (PDB:4J3K) as the search model. The initial models were rebuilt and refined by Coot [3] and Phenix. Structures were visualized using PyMOL (The PyMOL Molecular Graphics System, version 2.3.0).

(5) Chemical Cross-Link Assay

Protein solutions containing 40 μM of wild-type or mutated MERS-CoV N-NTD were incubated with glutaraldehyde at a final concentration of 1% v/v. The reaction was conducted at room temperature for 10 min and quenched with the addition of 1 M Tris-HCl (pH 7.5). The samples were then stored on ice and analyzed by sodium dodecyl sulfate-polyacrylamide gel electrophoresis (SDS-PAGE).

(6) Discovery of Orthosteric PPI Stabilizers for MERS N Protein

To screen for compounds that induce hydrophobic PPI between MERS N-NTDs, a model of dimeric MERS-CoV N-NTD without the H37 and M38 residues was used in virtual drug screening. The Sigma-Aldrich, Acros Organics, and ZINC drug databases were screened with LIBDOCK molecular docking software to obtain compounds acting on the N protein. The N protein binding pocket was represented by a set of spheres. Each compound in the database was docked in a pocket comprising W43. The hydrophobic complementarity between ligands and receptors was calculated with PLATINUM.

(7) Fluorescence Measurements

Fluorescence assays were performed in a buffer consisting of 50 mM Tris-HCl (pH 8.3) and 150 mM NaCl. One micromolar N protein was incubated either with the control buffer or each compound (10 μM) at 4° C. for 1 h. Tryptophan fluorescence was acquired with a Jasco FP-8300 fluorescence spectrometer (JASCO International Co. Ltd., Tokyo, Japan) at an excitation wavelength of 280 nm and an emission wavelength range of 300 to 400 nm.

(8) Thermostability Measurements

Thermostability assays were conducted in a buffer consisting of 50 mM Tris-HCl (pH 7.5) and 150 mM NaCl with a JASCO FP-8300 fluorescence spectrometer (JASCO International Co. Ltd., Tokyo, Japan). One micromolar N protein was incubated either with the control buffer or each compound (10 μM) at 4° C. for 2 h. UV absorbance vs. temperature profiles were acquired by ramping the temperature from 4 to 95° C. at 1° C./min, and the absorbance was recorded at 280 nm every 0.5 min.

(9) Determining Cytotoxic Concentration ($CC_{50}$) and Effective Concentration ($EC_{50}$) of Hit Compounds Vero E6 cells were infected by MERS-CoV or SARS-CoV2 (i.e., the virus of COVID-19) with multiplicity of infection (M.O.I)=0.1 and treated with lead compounds for 48 h. Cell viability was determined by the neutral red uptake assay. $CC_{50}$ and $EC_{50}$ were determined by % cell viability. $CC_{50}$ was determined for cells treated with drugs only. $EC_{50}$ was determined for MERS-infected cells after drug treatments.

(10) Small-Angle X-Ray Scattering (SAXS) Experiments

SAXS experiments were performed at the BL23A SAXS beamline at the TLS of NSRRC, using a monochromatic X-ray beam (λ=0.828 Å), with an integrated HPLC system of an Agilent-Bio SEC-3 300 Å column (Agilent Technologies, Inc. Santa Clara, CA). Protein samples (44 μM MERS-CoV N and MERS-CoV N:PSX-01 complex prepared by incubating the 44 μM native protein with 440 μM PSX-01) were prepared in a buffer consisting of 50 mM Tris-HCl (pH 8.5) and 150 mM NaCl on ice for 1 h. Then, a 100 μL aliquot was injected into the column at a flow rate of 0.02 mL/min. After passing through the column, the sample solution was directed into a quartz capillary (2 mm diameter) for subsequent buffer and sample SAXS measurement at 288K. The sample-to-detector distance of 2.5 m used covered a scattering vector q range of 0.01 to 0.20 $Å^{-1}$. Here, q is defined as $q=(4\pi/\lambda)\sin\theta$, with the scattering angle 2θ. Thirty-six frames were collected for each sample elution with an X-ray frame exposure time of 30 s. Frames of good data overlapping (namely, of low radiation damage effects) were merged for improved data statistics and analyzed to determine initial $R_g$ using PRIMUS (version 3.1). The P(r) distance distribution and D max were calculated from the experimental scattering curve using GNOM (version 4.1). An ensemble optimization method (EOM) analysis was performed through the EMBL Hamburg web interface. Modeling of the rigid body crystal structure was calculated and generated using CRYSOL (ATSAS Program Suite v. 2.8.2). The crystal structures of MERS-CoV NTD (PDB ID: 4UD1) and MERS-CoV NTD:PSX-01 (solved in this disclosure) and the CTD domain of MERS-CoV N protein (PDB ID: 6G13) were used as rigid bodies in EOM analysis. With the EOM analysis, 1,000 models were generated in the beginning as a structural pool. Selected from the SAXS profiles of the structural pool was an ensemble of models that could fit the experimental scattering curve with their linear combination. Tetrameric MERS-CoV NP conformations and 16-mer MERS-CoV:PSX-01 conformations were selected because their ensemble generated curves fit best to the experimental SAXS results.

(11) Viral Infection

Vero E6 cells (ATCC No.: CRL-1586) were seeded onto culture plates with complete Dulbecco's modified Eagle's medium (DMEM) and incubated overnight prior to infection. MERS-CoV (HCoV-EMC/2012) at a multiplicity of infection (M.O.I.) of 0.1 was added to the cells and incubated at 37° C. for 1 h, followed by washing thrice with phosphate-buffered saline (PBS) to remove the unattached virus. Fresh complete culture medium was then added to the plates.

(12) Plaque Assay

Vero E6 cells were seeded in 12-well plates and incubated overnight before the assays. Samples containing virus (e.g., MERS-CoV and SARS-CoV2) were serially diluted 10× with minimal essential medium (MEM), added to the wells, and incubated for 1 h with agitation every 15 min. After incubation, the inocula were removed and washed with PBS. An overlay medium comprising 2×MEM and 1.5% (w/v) agarose (1:1) was added to the wells, followed by incubation at 37° C. and 5% $CO_2$ for 3 days. The plates were fixed with 10% (v/v) formalin containing 0.2% (w/v) crystal violet, and the plaques were counted.

(13) RT-qPCR

Total RNA of infected Vero E6 cells was extracted with the RNeasy Mini Kit (Qiagen, Hilden, Germany) according to the manufacturer's instructions. Reverse transcription and PCR amplification were performed with an iTaq Universal One-Step RT-qPCR Kit (Bio-Rad Laboratories, Hercules, CA). Real-time PCR was performed in a StepOnePlus Real-Time PCR System (Applied Biosystems, Foster City, CA). The primer pairs used to amplify the viral RNA were as follows:

```
GAPDH-F:
                                   (SEQ ID NO. 12)
5'-GAAGGTGAAGGTCG-GAGTC-3';

GAPDH-R:
                                   (SEQ ID NO. 13)
5'-GAAGATGGTGATGGGATTTC-3';
```

-continued

```
MERS-CoV-F:
                                   (SEQ ID NO. 14)
5'-CCACTACTCCCATTTCGTCAG-3';

MERS-CoV-R:
                                   (SEQ ID NO. 15)
5'-CAGTATGTGTAGTGCGCATATAAGCA-3'.
```

The MERS RNA levels were normalized to that of GAPDH and compared between MERS-CoV groups at 24 hours post infection (h.p.i.) and at 48 h.p.i.

(14) Immunofluorescence Assay

Vero E6 cells were seeded in eight-well chamber slides and incubated overnight prior to infection with MERS-CoV at M.O.I.=0.1. The cells were fixed with 4% (v/v) paraformaldehyde for 20 min at 4° C., followed by permeabilization in 0.1% (v/v) Triton X-100 for 10 min. Then, 7.5% (v/v) bovine serum albumin (BSA) was used as a blocking buffer for 30 min at 37° C. Anti-MERS-CoV N primary antibody (1:500 dilution; Sino Biological Inc., Beijing, China) was used to stain the virus. The cells were incubated overnight, washed thrice with PBS, and incubated with Alex Fluor 568 anti-rabbit secondary antibody (1:1000 dilution; Thermo Fisher Scientific, Waltham, MA) for 1 h at room temperature. 4',6-Diamidino-2-phenylindole (DAPI) was added during the PBS wash. MERS nucleocapsid expression was examined under a confocal microscope (LSM-700; Carl Zeiss AG, Oberkochen, Germany).

Example 1: Structure of the N-Terminal Domain of the MERS-CoV N Protein

The crystal structure of MERS-CoV N-NTD was determined by molecular replacement (MR) using the structure of HCoV-OC43 N-NTD (PDB ID: 4J3K) as the search model. The final structure was refined to R-factor and R-free values of 0.26 and 0.29, respectively, at a resolution of 2.6 Å, as shown in Table 2 below.

TABLE 2

Crystallographic data collection and refinement statistics

| Data collection | NSRRC BL13B1 | NSRRC BL13C1 | SP44XU, Spring8 |
|---|---|---|---|
| Crystal | Native | MERS: P1 | MERS: PSX-01 |
| Wavelength (Å) | 1 | 0.97622 | 0.9 |
| Space group | P21 | P21 | P21 |
| Cell dimensions | | | |
| a, b, c (Å) | 35.601, 109.645, 91.993 | 35.440, 109.897, 91.526 | 35.489, 108.477, 91.595 |
| α, β, γ (°) | 90, 101.23, 90 | 90, 90, 101.103 | 90, 90, 101.160 |
| Resolution range (Å) | 30.00-2.63 (2.73-2.63) | 30.00-3.09 (3.20-3.08) | 30.00-2.77 (2.87-2.77) |
| Unique reflections | 19199 (1597) | 11929 (1009) | 17364 |
| Completeness (%) | 94.5 (91.4) | 96.1 (96.9) | 99.5 (99.4) |
| Mean I/σ (I) | 18.897 (3.304) | 9.143 (2.500) | 31.387 (99.4) |
| R-merge | 0.096 (0.494) | 0.141 (0.482) | 0.072 (0.477) |
| Redundancy | 7.1 (5.9) | 3.5 (3.4) | 6.3 (7.3) |
| Refinement | | | |
| R-work/R-free | 28/28.98 | 28.18/29.93 | 23.15/27.07 |
| Number of atoms | 3546 | 3498 | 3680 |
| Macromolecules | 3445 | 3477 | 3549 |
| Ligands | n/a | 21 | 21 |
| Water | 101 | 0 | 110 |
| Protein residues | 543 | 445 | 453 |
| Average B-factor | 40.6 | 54.09 | 35.33 |
| Macromolecules | 40.7 | 54.14 | 35.41 |
| Ligands | n/a | 45.41 | 38.46 |
| Solvent | 37.9 | n/a | 32.26 |
| RMSD | | | |
| Bonds lengths (Å) | 0.013 | 0.012 | 0.008 |
| Angles (°) | 1.59 | 1.67 | 1.13 |

TABLE 2-continued

| Crystallographic data collection and refinement statistics | | | |
|---|---|---|---|
| Data collection | NSRRC BL13B1 | NSRRC BL13C1 | SP44XU, Spring8 |
| Ramachandran plot | | | |
| Favored (%) | 98.35 | 98.14 | 98.84 |
| Outliers (%) | 0 | 0 | 0 |
| Clash score | 15.7 | 15.01 | 25.53 |

Each asymmetric unit contained four N-NTD molecules assembled into two identical dimers with an overall root-mean-square deviation (RMSD) of 0.28 Å between the dimers. The monomers shared a similar structural core preceded by a flexible region. The core consisted of a five-stranded antiparallel β-sheet sandwiched between loops arranged in a right-handed, fist-shaped structure conserved among the CoVs.

In the structure of this disclosure, however, the loop connecting strands β2 and β3 protruding out of the core into other CoV N proteins was absent. That is to say, the structure used herein was atypically dimeric.

FIG. 1A showed the details of the interactions in the MERS-CoV N protein dimer. According to the amino acid composition of the binding site on monomer 2, the dimeric interface was divided into two areas: one located on the N-terminus flexible region; and the other one located on the loop between β4 and β5 of the N protein. Dimerization was mediated mainly by vector-fusion residues interacting with the conserved hydrophobic regions on the core structure (the first area) along with the residues surrounding it (the second area).

Figure 1B:
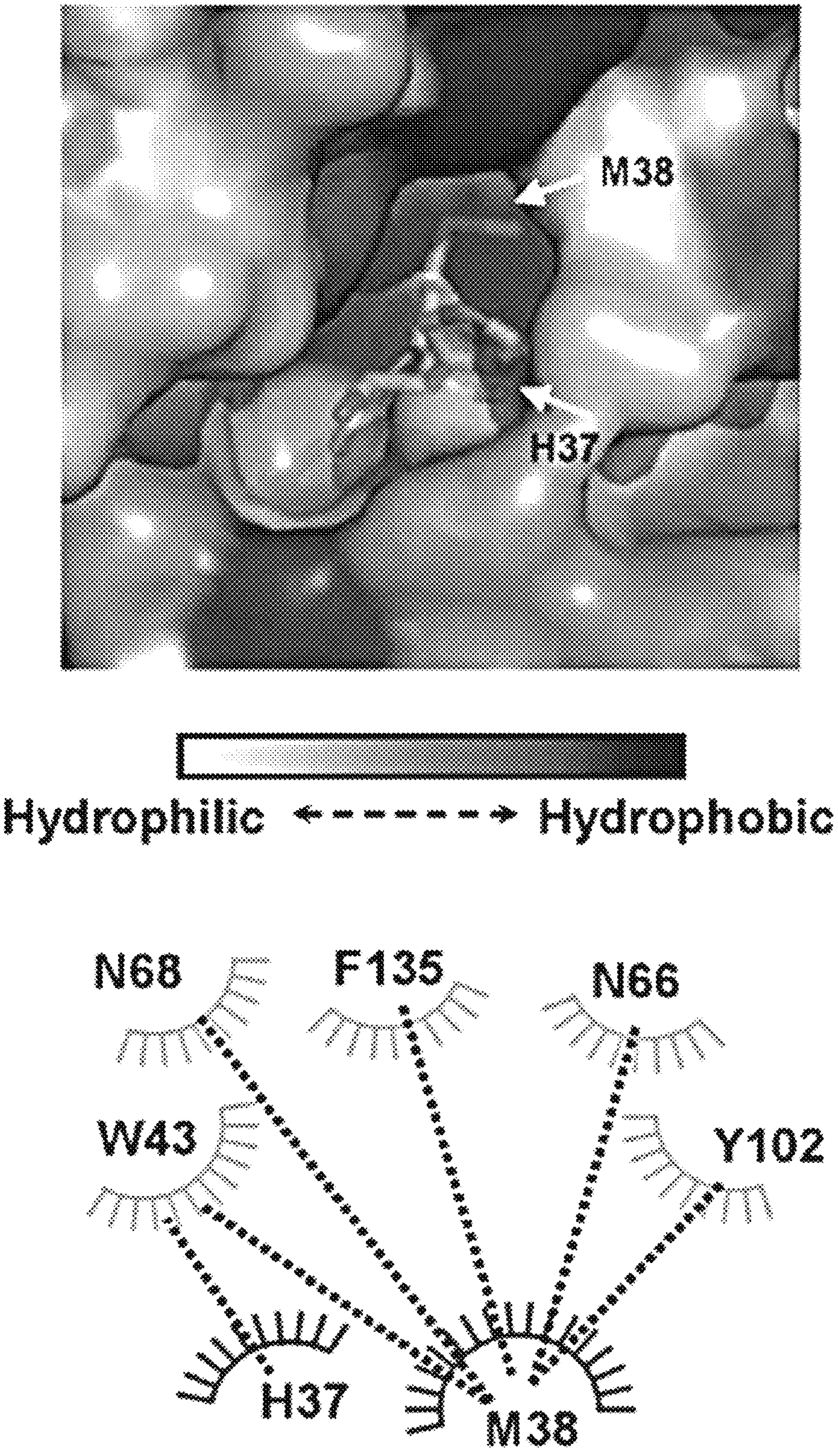

In the first area, W43, N66, N68, Y102, and F135 of monomer 1 generated a conserved hydrophobic pocket permitting the side chain of M38 of monomer 2 to enter this hole by a hydrophobic contact as illustrated in FIG. 1B. H37 and N39 of monomer 2 were packed against W43 and F135 of monomer 1, respectively, and contributed to the hydrophobic interaction. The side chains of N39 of monomer 2 formed one hydrogen bond with the N68 backbone in monomer 1 at a distance of 2.6 Å. The second area was relatively more hydrophilic.

Figure 1C:
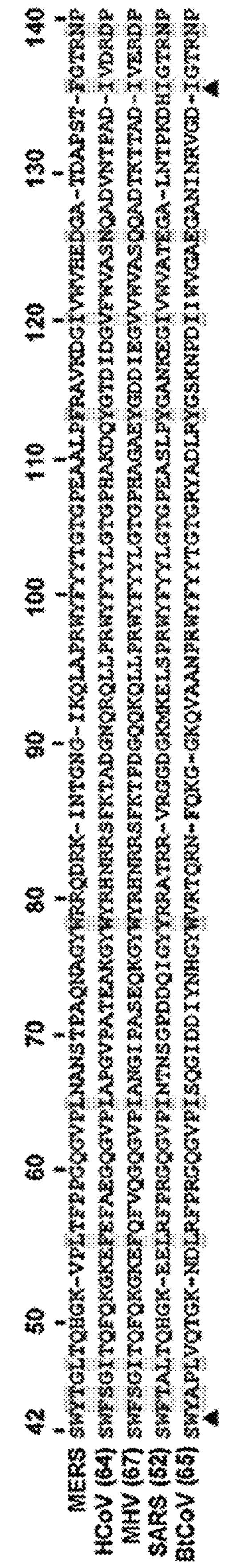

The main chain oxygens of G104, F135, and T137 of monomer 2 formed three hydrogen bonds with the side chains of Q73 and T134 of monomer 1 at distances of 3.8, 3.2, and 3.7 Å, respectively. The side chain of N139 on monomer 2 formed a hydrogen bond with the main chain oxygen of T137 on monomer 1 at a distance of 3.6 Å (referring also to FIG. 1C). The interactions of the first and second areas comprise buried surface areas (BSA) of 289 and 103 $Å^2$, respectively. The small surface area buried at the interface accounts for about 5 kcal/mol binding energy, which translates to a dissociation constant of about 200 mM. Thus, the dimer described here was unique in that it was non-native and relied on vector-fusion residues (H37 and M38) to maintain its dimeric status. This property may also explain why the present structure has an oligomeric status different from previously reported structures for the CoV N protein.

Figure 1D:
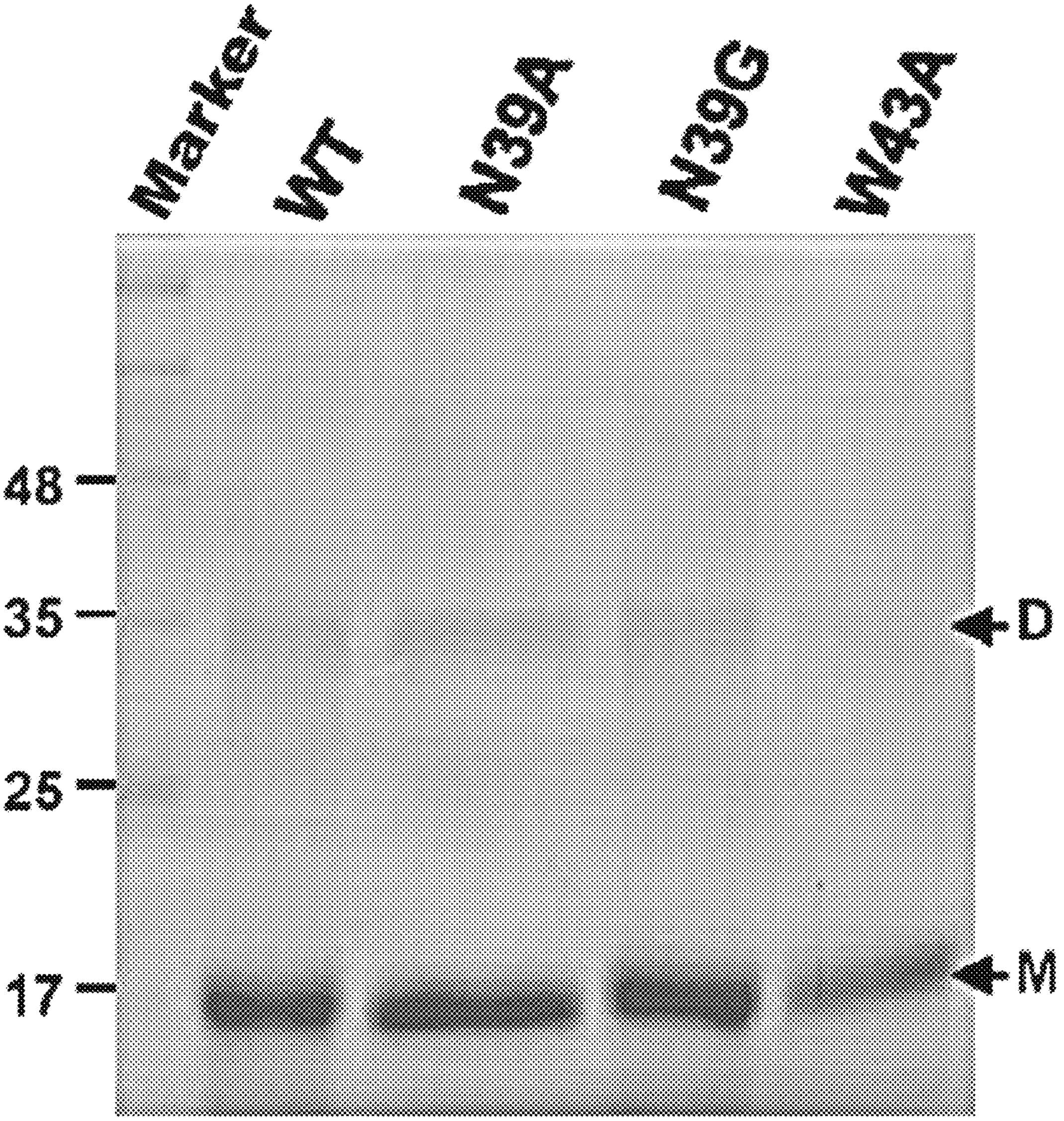

The cross-linking experiments were used to analyze the oligomeric capacity of MERS N-NTD containing the vector-fusion residues in solution. MERS N-NTD had a dimeric conformation in solution. Such structure indicated that W43 involved in forming the hydrophobic pocket accommodating the vector-fusion residues and, therefore, mediated the N-NTD dimer formation. As shown in FIG. 1D, the W43A mutation significantly reduced the oligomeric tendency of N-NTD. This further supported that the "exogenous residues" encoded by the vector backbone mediated the formation of the non-native dimer.

Figure 1E:
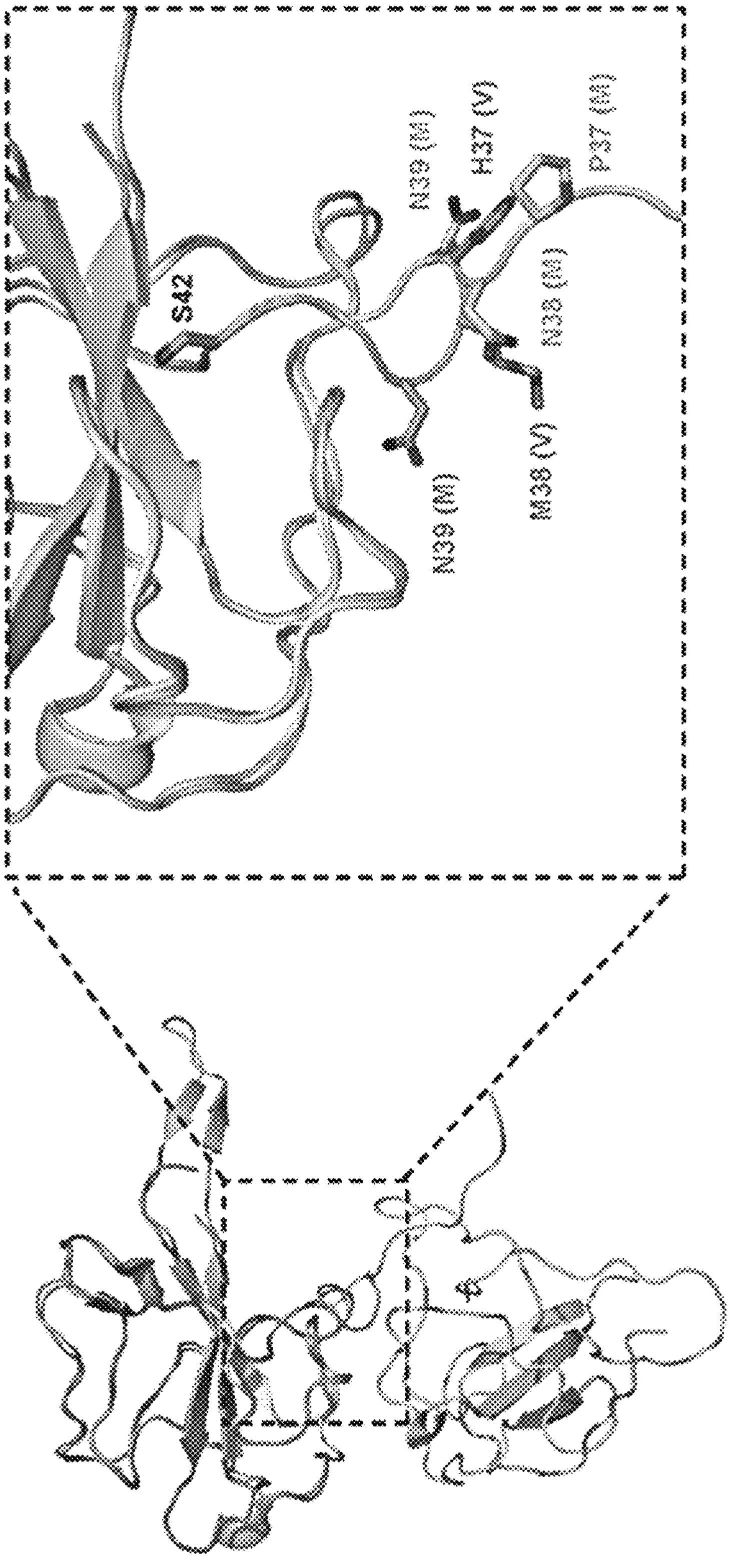

The previously published structure of MERS-CoV N-NTD (PDB ID: 4ud1) containing a native N-terminal flexible region was further superimposed with the dimer structure herein. It was shown that the side chain of N38 in the native structure could not interact with the hydrophobic pocket as the former was hydrophilic and short (FIG. 1E). Thus, it may be possible to utilize small compounds to replace the vector-fusion residues and stabilize the PPI through hydrophobic interactions.

Example 2: Direct Targeting of the Non-Native Dimer Interface for Antiviral Screening In this example, a structure-based virtual screening was performed by targeting W43 in the hydrophobic pocket of the N-NTD dimeric interface. H37 and M38 were removed from the template to identify compounds that could replace the vector-fusion residues and, therefore, contribute to the stabilizing effect. The highest-scoring hits were determined based on shape complementarity, the presence of aromatic moieties, and the ability to stack onto W43 of N-NTD. Because the formation of the non-native dimers was primarily mediated by hydrophobic interactions, the hydrophobic complementarity between the acquired ligands and N-NTD in the form of the lipophilic match surface ($S_{L/L}$) was further considered. The ability of the drug to permeate cells was also considered by aiming for lower topological polar surface areas (TPSA). The results were reported in Table 3 below.

TABLE 3

| W43 docking pose with chemical structures, docking scores, and biochemical properties of 17 potential hits | | | |
|---|---|---|---|
| Compound Name | LibDock Score | TPSA ($Å^2$) | $S_{L/L}$ ($Å^2$) |
| 5-Benzyloxygramine (PSX-01) | 121.445 | 28.26 | 59.87 |
| 5-(9H-xanthen-9-yl)-1,3,4-oxadiazol-2-ol | 120.754 | 68.13 | 34.3 |
| Aspartame | 120.453 | 118.72 | 35.38 |

TABLE 3-continued

W43 docking pose with chemical structures, docking scores, and biochemical properties of 17 potential hits

| Compound Name | LibDock Score | TPSA ($Å^2$) | $S_{L/L}$ ($Å^2$) |
|---|---|---|---|
| Benzyl 2-(hydroxymethyl)-1-indolinecarboxylate (P1) | 113.82 | 49.77 | 59.24 |
| 2-[(7-Hydroxy-4-methyl-2-ox-chromen-8-yl)methyl-methylamino]acetic acid | 112.677 | 90.98 | 32.02 |
| 3,3'-Dipicolyamine | 104.66 | 37.81 | 10.89 |
| 1-Cyclohexyl-N-((1-methylpyrrolidin-2-yl)methyl)ethanamine | 104.575 | 15.27 | 55.13 |
| 5-(4-Chloro-pyrazol-1-ylmethyl)-furan-2-carboxylic acid | 103.727 | 68.27 | 43.54 |
| L-Carnosine | 102.696 | 121.10 | 0 |
| 2-[2-(2-Chloroethoxy)ethyl]isoindole-1,3-dinone | 101.784 | 48.31 | 33.29 |
| 4-(2-Morpholin-4-ylethoxy)aniline | 101.191 | 47.73 | 28.86 |
| 3,3'-Sulfonyldianiline | 100.829 | 86.19 | 36.52 |
| 5-(1H-pyrazol-1-ylmethyl)-2-furoic acid | 99.7464 | 68.27 | 41.71 |
| 4-(2,2-Dimethoxyethyl)-5-phenyl-4H-1,2,4-triazole-3-thiol | 99.6227 | 52.09 | 41.9 |
| N-{[5-(2-furyl)-1,3,4-oxadiazol-2-yl]methyl}-N-propylamine | 97.9875 | 64.09 | 45.89 |
| Etodolac (P2) | 85.4327 | 62.32 | 52.85 |
| Diethyl 1-benzylpyrrolidine-2,5-dicarboxylate | 84.966 | 55.85 | 50.82 |

Based on the above criteria, three candidate compounds were finally chosen for further study. Benzyl-2-(hydroxymethyl)-1-indolinecarboxylate (P1) and 5-benzyloxygramine (PSX-01) had higher $S_{L/L}$ and docking scores and lower TPSA. The clinical drug etodolac (P2) had a comparable $S_{L/L}$ but a lower docking score, and was also selected as a candidate.

As a result, PSX-01 induced a comparatively larger blue shift in the intrinsic N-NTD fluorescence spectrum, indicating that the microenvironment surrounding the tryptophans of the protein increased in rigidity and hydrophobicity in the presence of PSX-01.

Figure 2A:
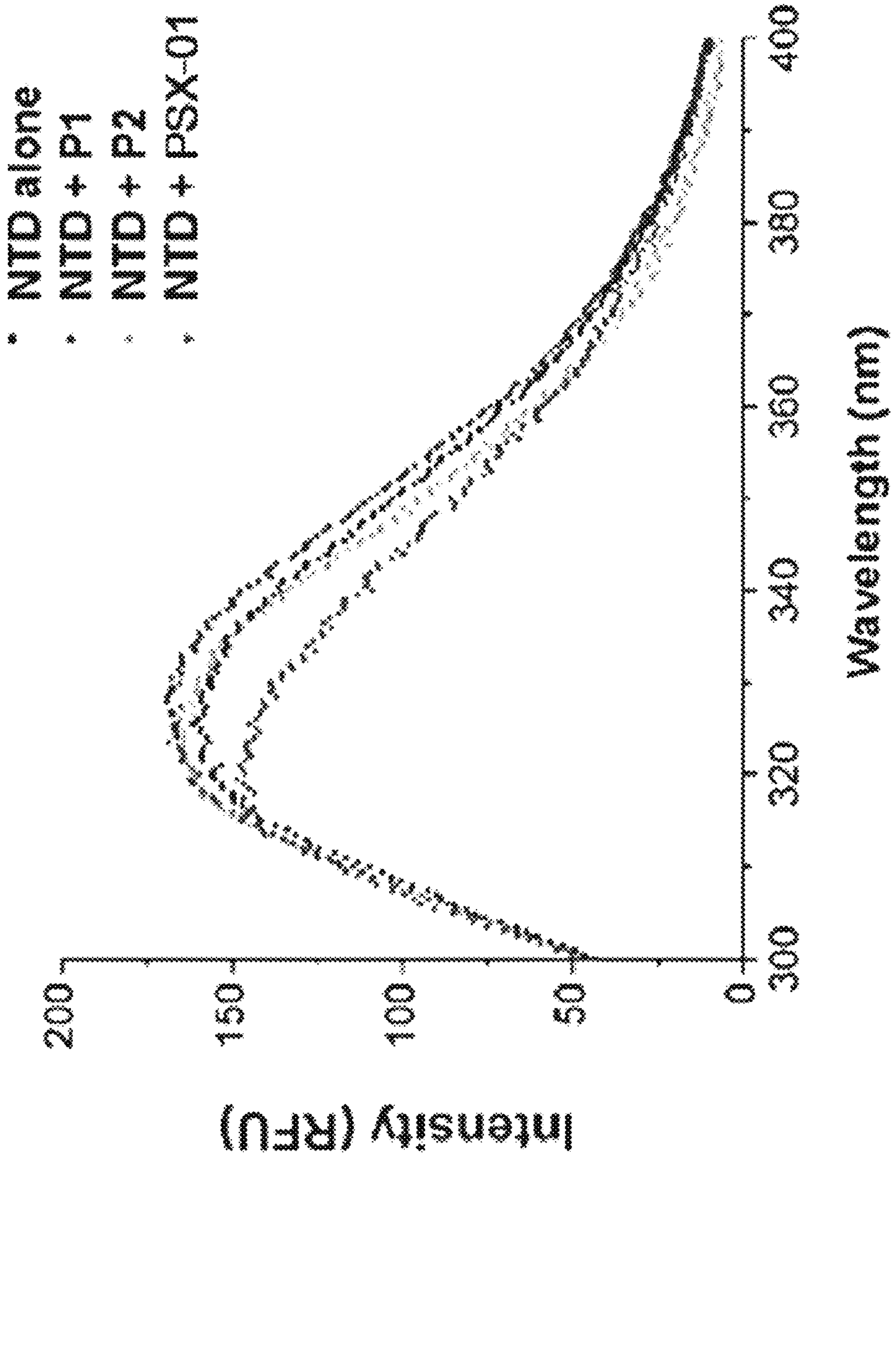
FIGS. 2A and 2B show the results of conformation (FIG. 2A) and stability analyses (FIG. 2B), which are performed based on the fluorescence (FL) spectra of NTD (1 μM) incubated with P1, P2 or PSX-01 (10 μM) for 1 h with a buffer containing 50 mM Tris-HCl (pH 8.3) and 150 mM NaCl. RFU: relative fluorescence unit.
Figure 2B:
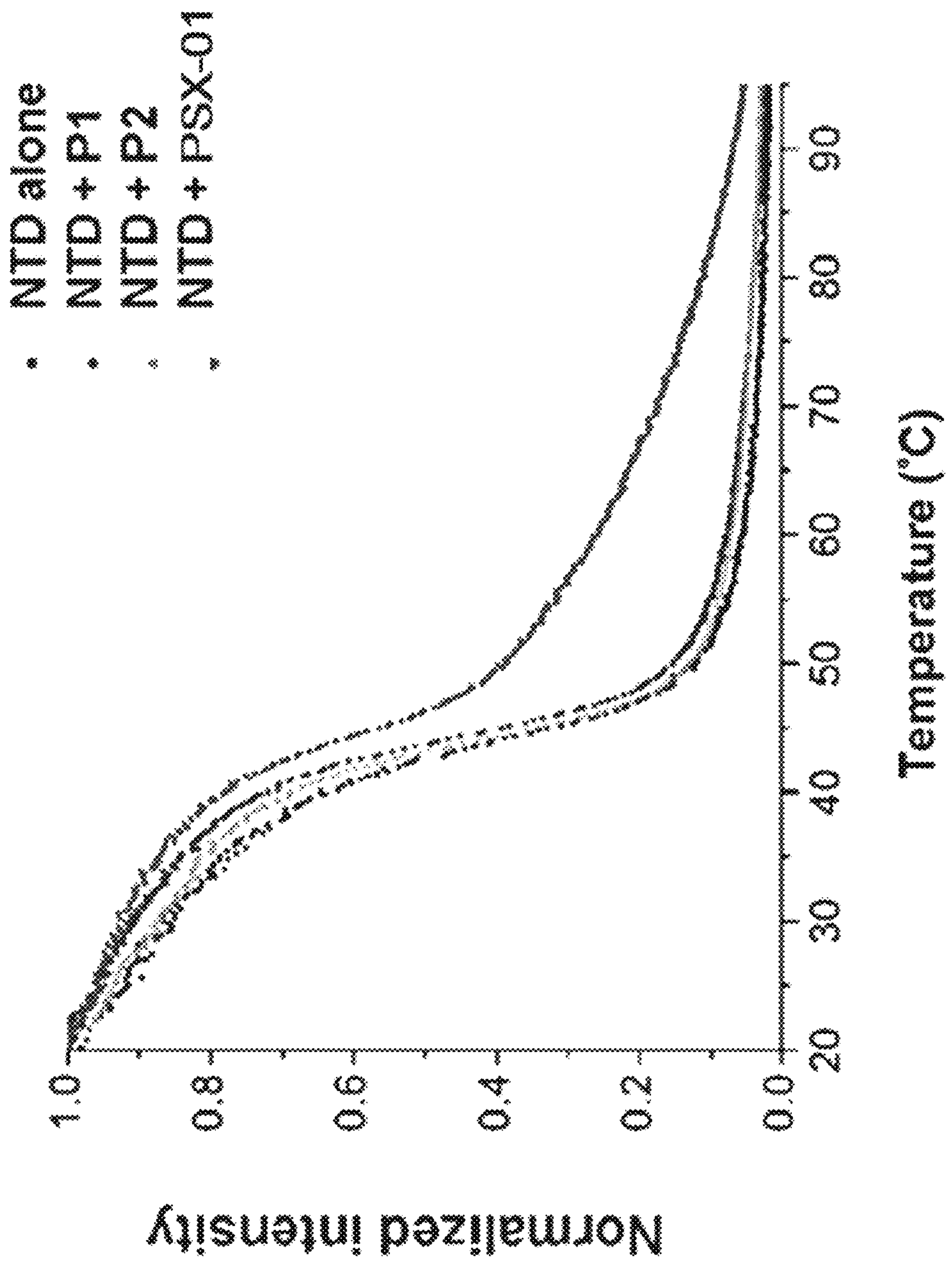

The result also indicated that PSX-01 bound more tightly to the N protein than P1 or P2 by interacting with the W43 pocket (referring to FIG. 2A). Fluorescent thermal stability assays disclosed that the N-NTD denaturation melting temperature had increased from 42 to 45° C. when PSX-01 was added. The sigmoidal melting curve for MERS-CoV N-NTD changed in the presence of PSX-01. The delay in protein denaturation suggests that PSX-01 stabilized the MERS-CoV N-NTD dimer structure (FIG. 2B). Then, the cytotoxic concentration ($CC_{50}$) and effective concentration ($EC_{50}$) was measured for each compound using Vero E6 cells infected with MERS-CoV.

Table 4 below showed that PSX-01 had a favorable therapeutic index (TI) among the lead compounds tested in this study. Therefore, PSX-01 could be a candidate inhibitor against MERS-CoV.

TABLE 4

$CC_{50}$, $EC_{50}$ and therapeutic indexes of lead compounds
Quantal dose - response relationship (μM)

| Compound | $CC_{50}$[a] | $EC_{50}$[b] | TI[c] ($CC_{50}/EC_{50}$) |
|---|---|---|---|
| P1 | 459.69 | >100 | NA[d] |
| P2 | 569.77 | >100 | NA[d] |
| PSX-01 | 805.32 | 32.1 | 25.1 |

[a]$CC_{50}$: Half maximal cytotoxic concentration.
[b]$EC_{50}$: Half maximal effective concentration.
[c]TI: Therapeutic index.
[d]NA: Nonavailable.

Example 3: Structural Model of PSX-01-Induced MERS-CoV N Protein Aggregation

Figure 3A:
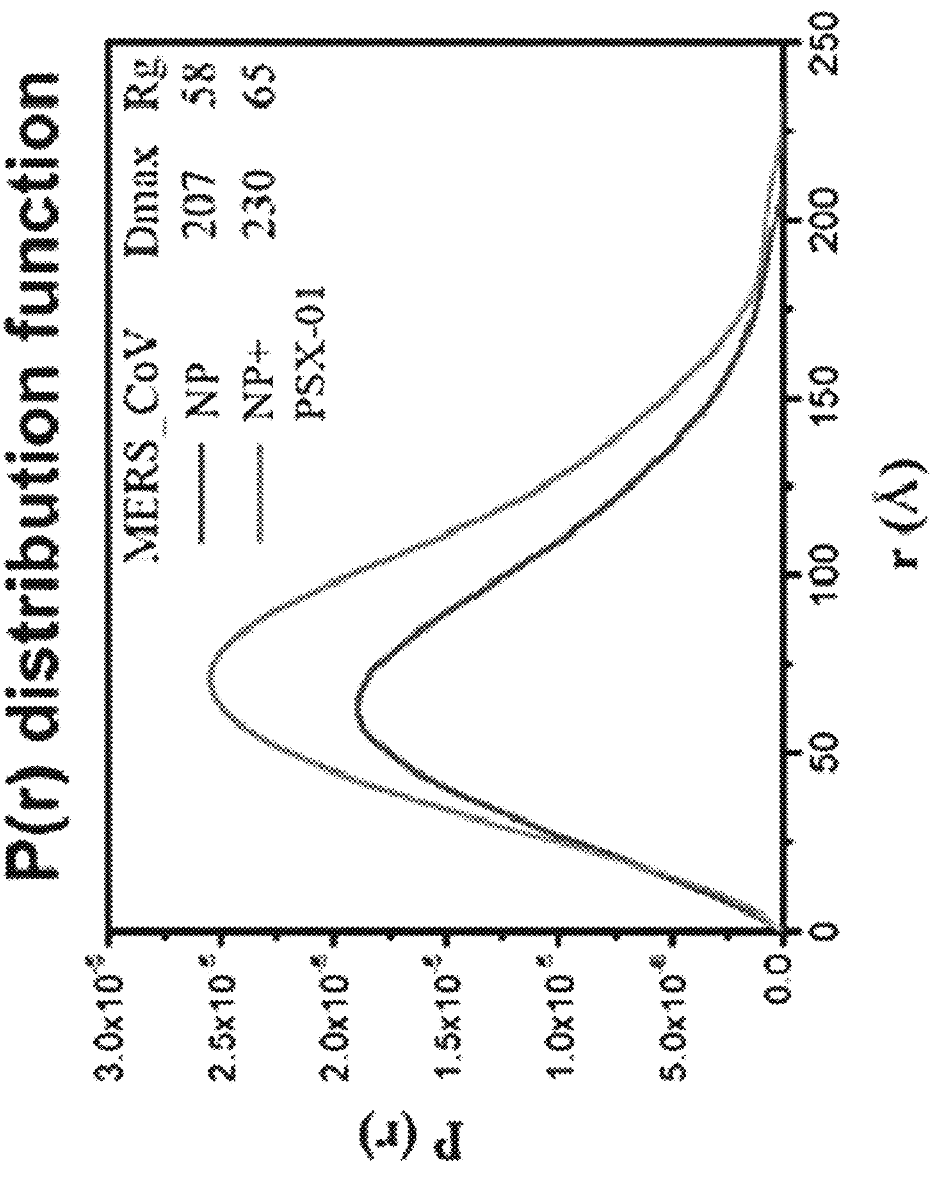
FIGS. 3A to 3H show PSX-01-induced abnormal aggregation on the full-length MERS-CoV N protein.

In this example, SAXS was used to assess the effects of PSX-01 on the full-length MERS-CoV N protein structure. The fitted distance distribution function of the protein with and without PSX-01 were shown in FIG. 3A. PSX-01 increased the maximum dimension ($D_{max}$) and radius of gyration ($R_g$) of the protein from 207 to 230 Å and from 58 to 65 Å, respectively. Thus, the size of the MERS-CoV N protein in solution was altered upon binding to PSX-01.

Figure 3B:
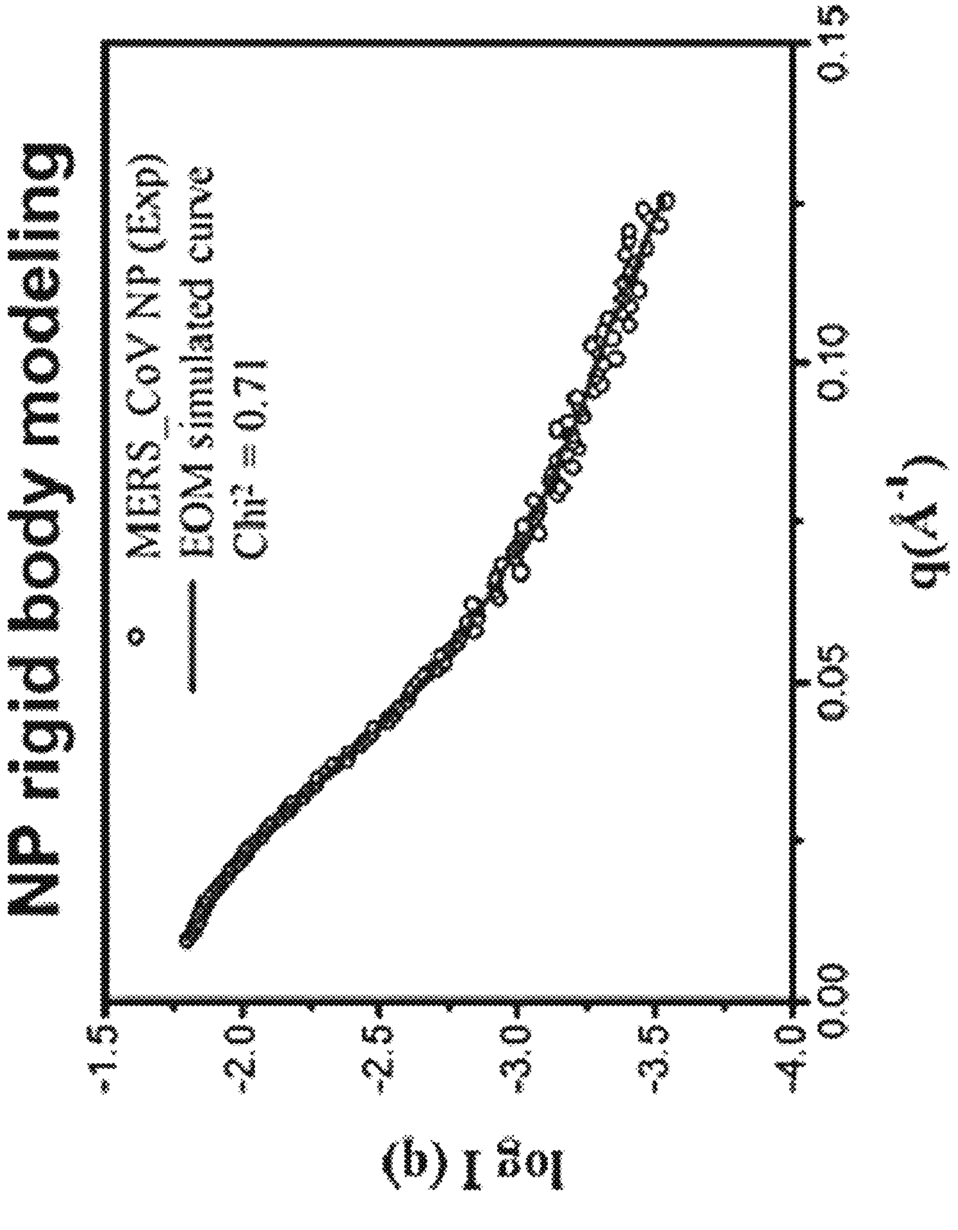
Figure 3C:
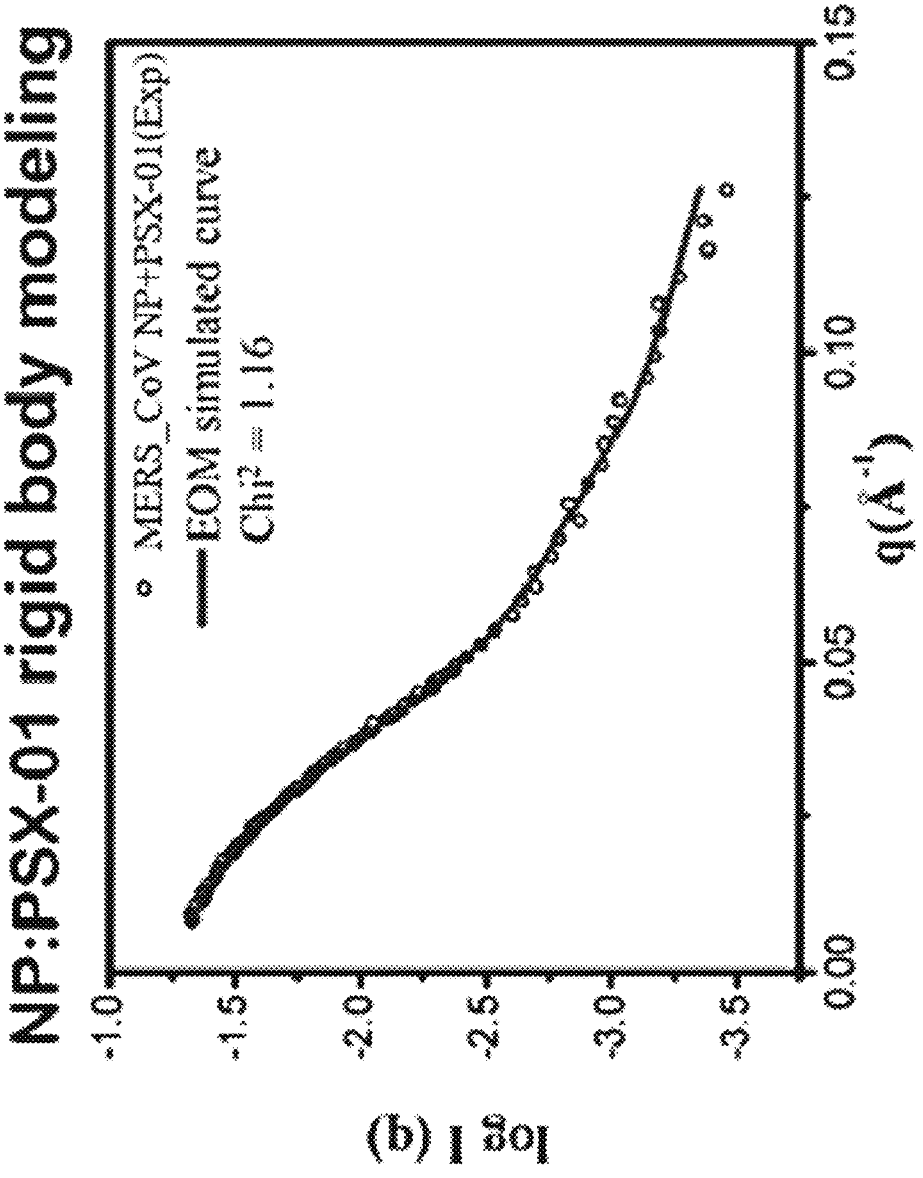
Figure 3D:
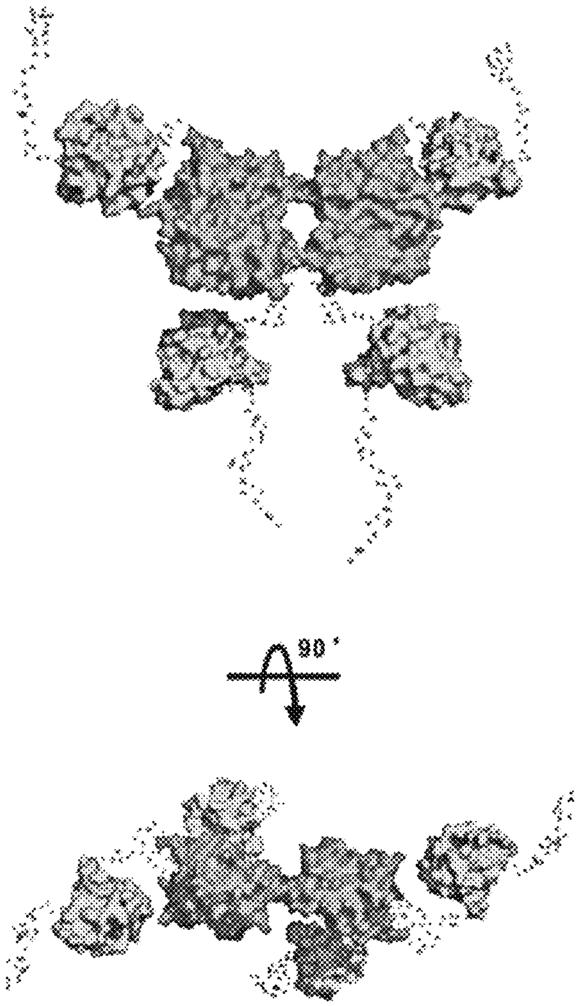
Figure 3E:
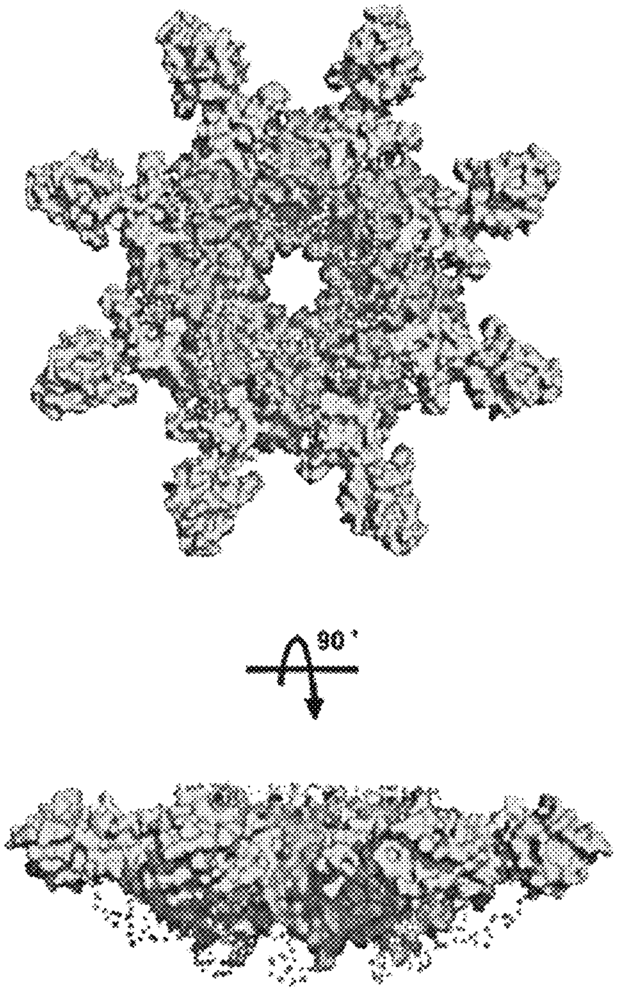

The presence of multiple intrinsically disordered regions in the N protein precluded the determination of its structure by X-ray crystallography. Instead, rigid body modeling of the SAXS data with the N-terminal domain (NTD; solved in this disclosure) and the C-terminal domain (CTD, PDB ID: 6G13) was used. In this way, structural models for the free N protein and its complex with PSX-01 were obtained (FIGS. 3B and 3C). Excellent fits were obtained. Representative structural models for the full-length protein without and with PSX-01 were shown in FIGS. 3D and 3E, respectively. The free N protein formed a tetramer through CTD with the NTD freely hanging in solution (FIG. 3D). The NP-PSX-01 complex formed a compact hexadecamer with a sunburst configuration (FIG. 3E).

Figure 3F:
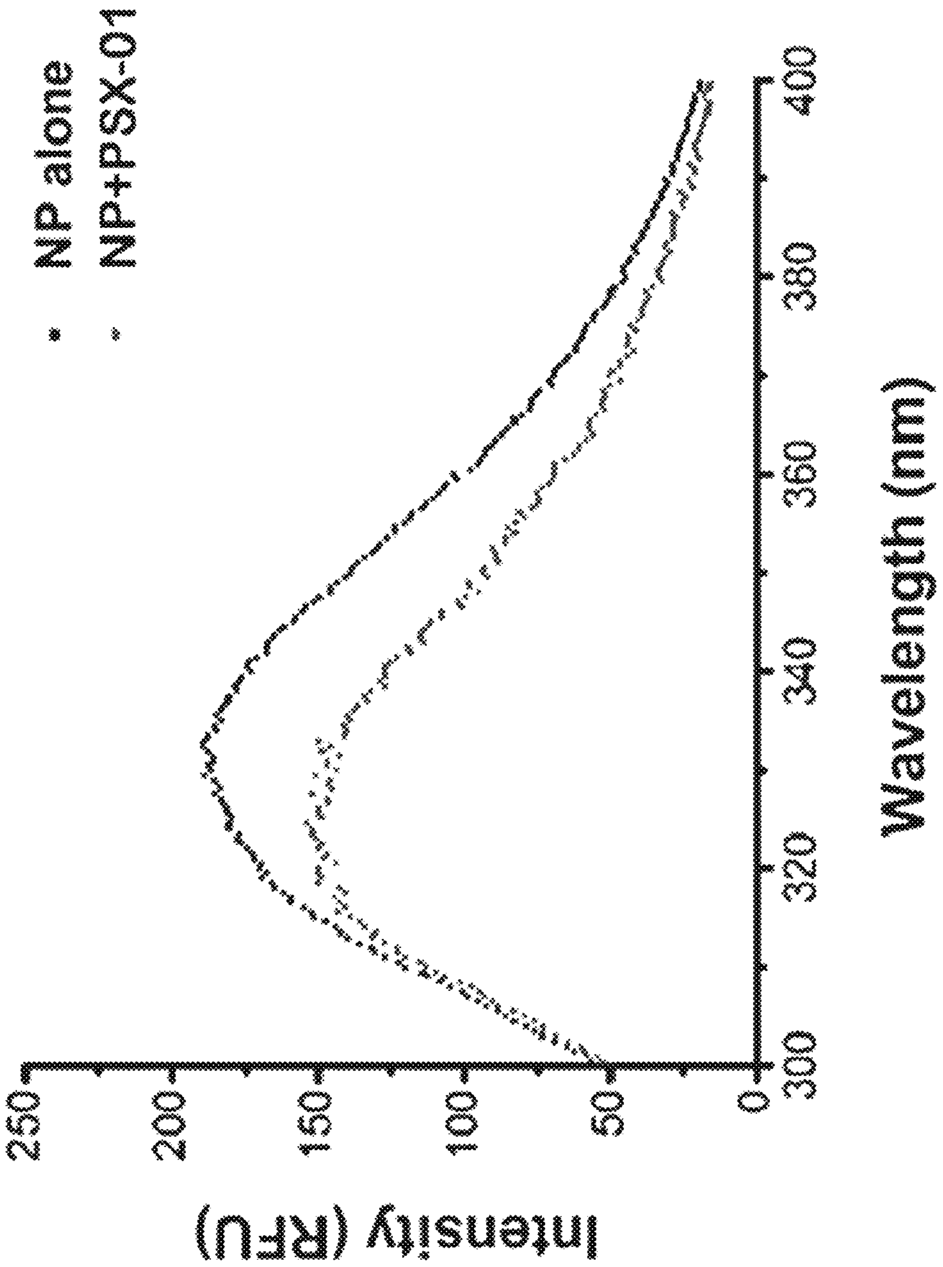
Figure 3G:
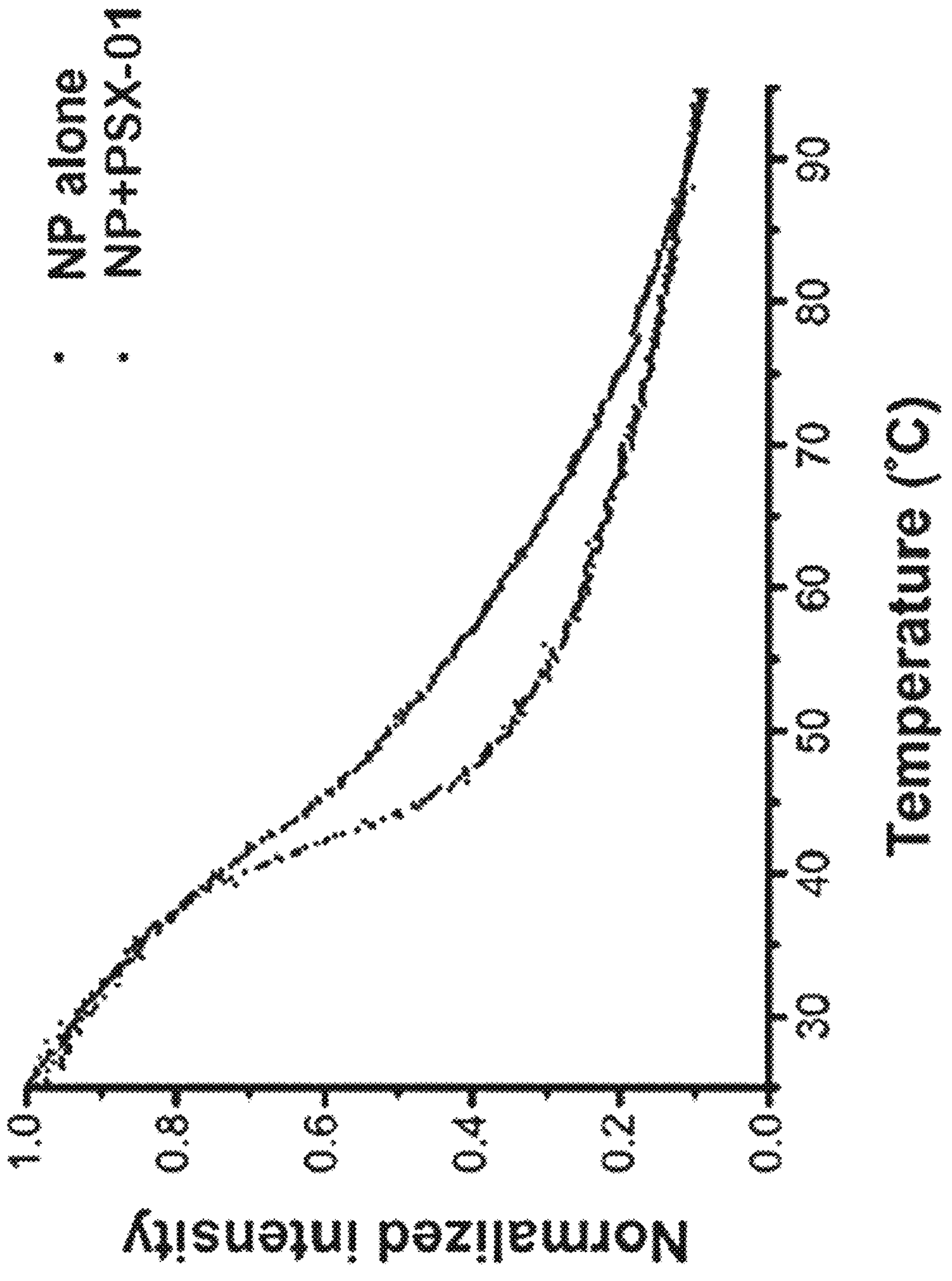

The CTDs formed a central ring, and the non-native NTD dimers formed "spikes" protruding from the ring. Consistent with ligand-induced aggregation, a "blue shift" was observed in the fluorescence spectrum of the full-length MERS-CoV N protein in the presence of PSX-01 (FIG. 3F). The addition of PSX-01 also delayed N protein thermal denaturation and changed the shape of the denaturation curve, further suggesting that large protein aggregates formed in the presence of PSX-01 (FIG. 3G). The structure explains how N-NTD dimerization decreased MERS-CoV viability. The N protein packages the viral genome into an RNP complex. Several models for N-CTD dimer assembly have been proposed for the formation of filamentous RNPs.

Figure 3H:
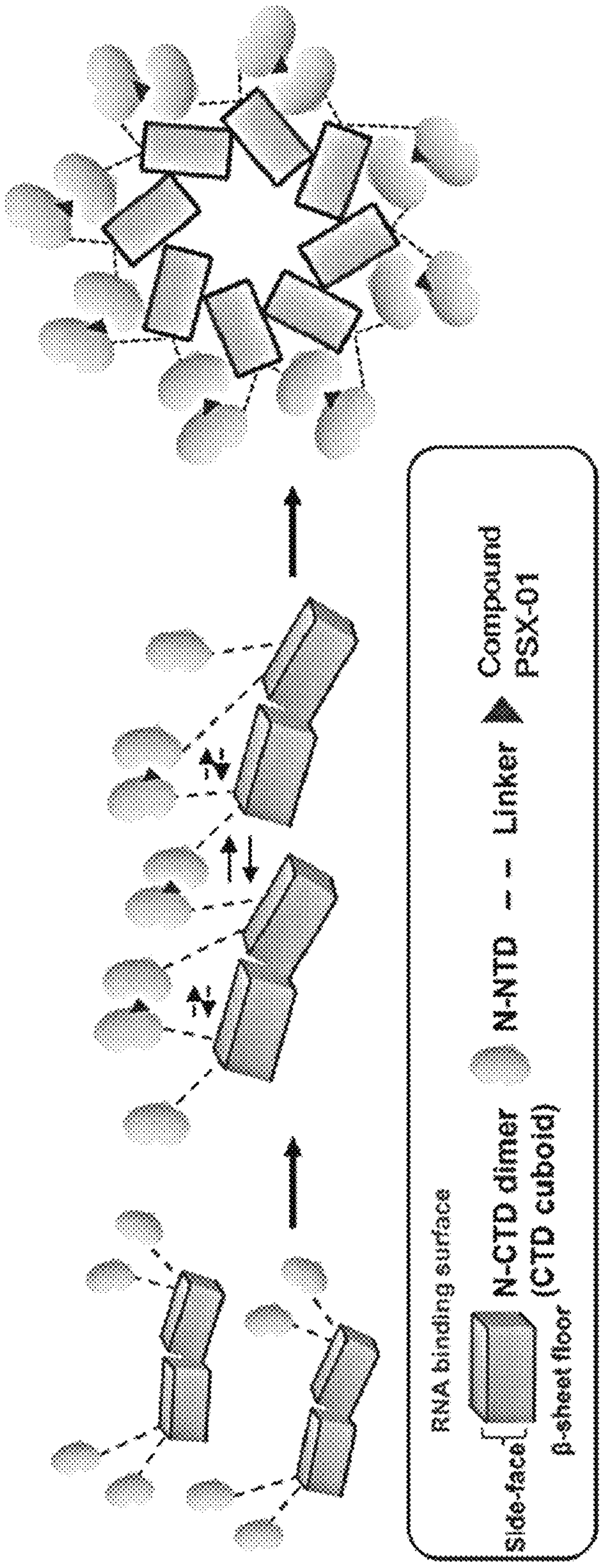

All of the proposed interfaces between N-CTD dimers occurred on the side-faces of the CTD cuboid perpendicular to the proposed RNA-binding surface (FIG. 3H). Combinatorial use of any region on the side-faces of the CTD dimer cuboid may facilitate manipulation of the RNP length and curvature without obstructing the RNA-binding surface. However, the SAXS results indicated that N-CTD aggregation occurred on the R-sheet floor of the CTD cuboid. For this reason, the RNA-binding surface of the CTD was occluded by the neighboring CTD on the ring and by the non-native NTD dimer making direct contact with the CTD (FIG. 3H). In addition, the CTD cuboids in the aggregation naturally formed a topologically closed octamer, leaving no open ends for further addition of CTD cuboids to form a long filamentous RNP. Both the loss of the RNA-binding surface and the inability to incorporate further N protein molecules beyond an octamer may inhibit the formation of the RNP. Therefore, PSX-01 may inhibit MERS-CoV RNP formation by inducing N protein aggregation.

Example 4: PSX-01 Inhibits MERS-CoV by Inducing N Protein Aggregation

Figure 4A:
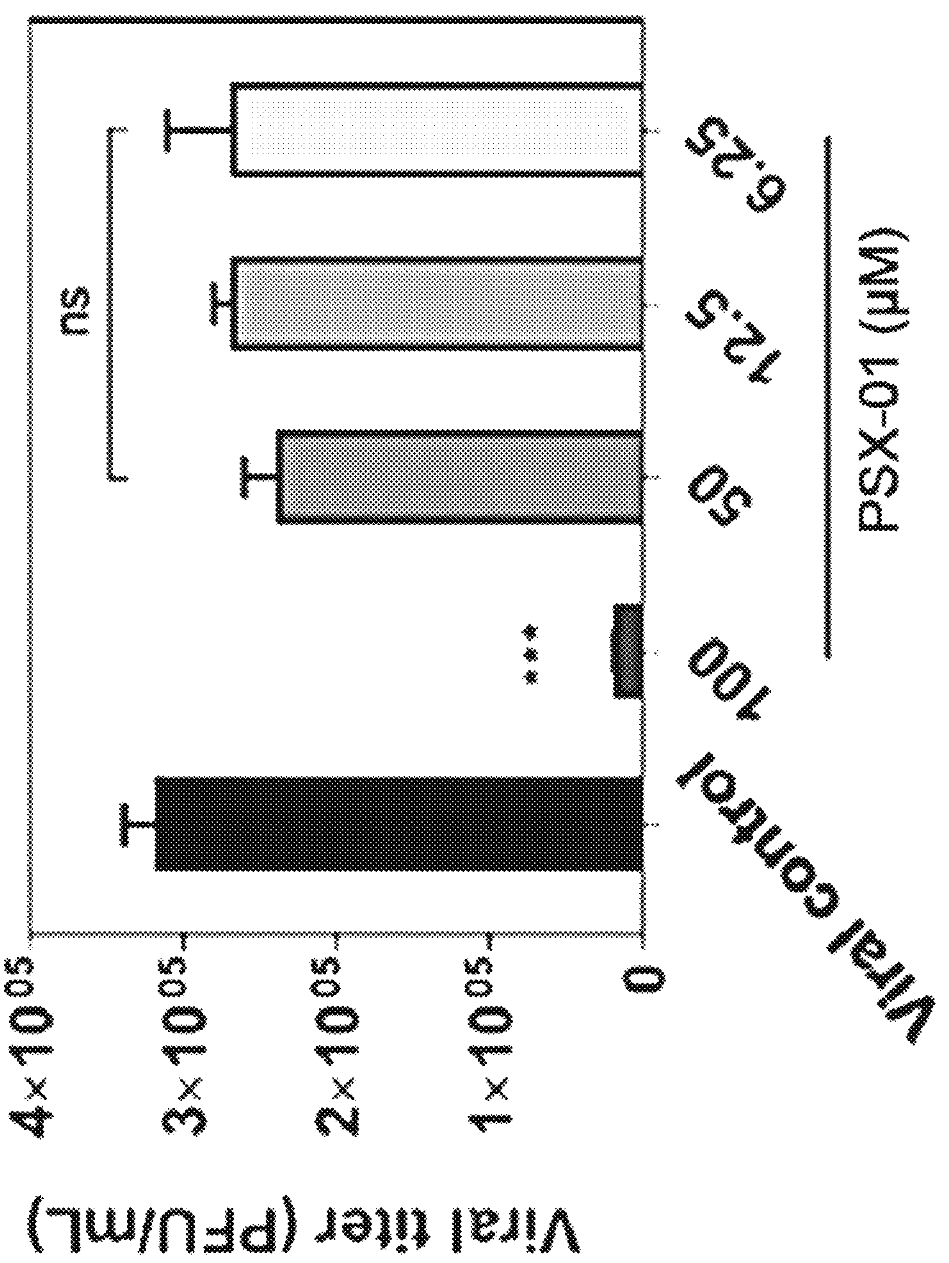
FIGS. 4A to 4C show that compound PSX-01 was a potential inhibitor against MERS-CoV.
Figure 4B:
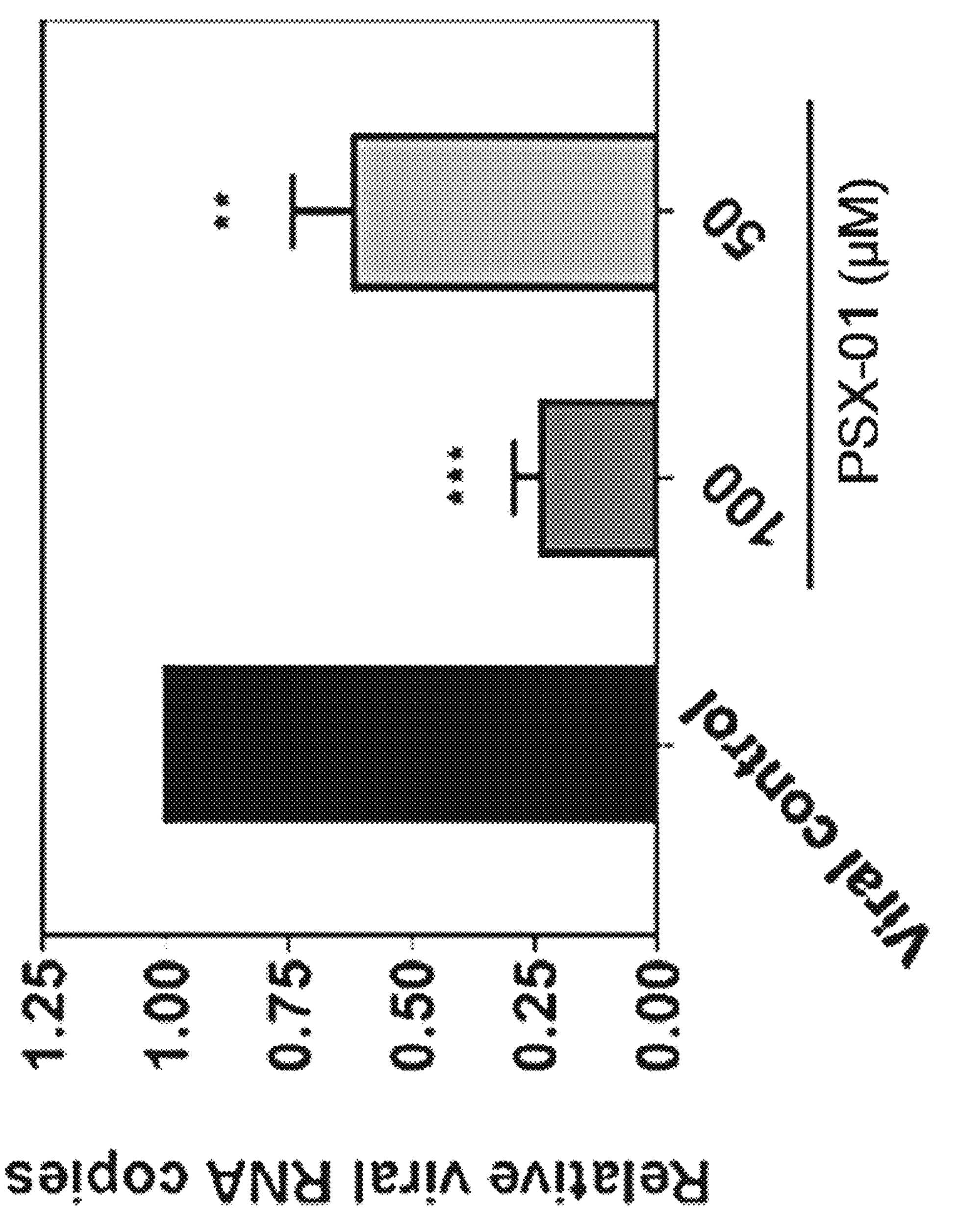

To determine the anti-MERS-CoV activity of PSX-01 in the cell, the effects of PSX-01 incubation on extracellular viral titers and intracellular viral RNA levels were assessed by plaque assays on Vero E6 cells (FIG. 4A) and by RT-qPCR (FIG. 4B), respectively. At 50 μM, PSX-01 affected the viral titer after 48 h and suppressed viral RNA replication by 40%. At 100 μM, PSX-01 halted both viral production and replication after 48 h. This result proved the capacity of PSX-01 as an antiviral compound.

Figure 4C:
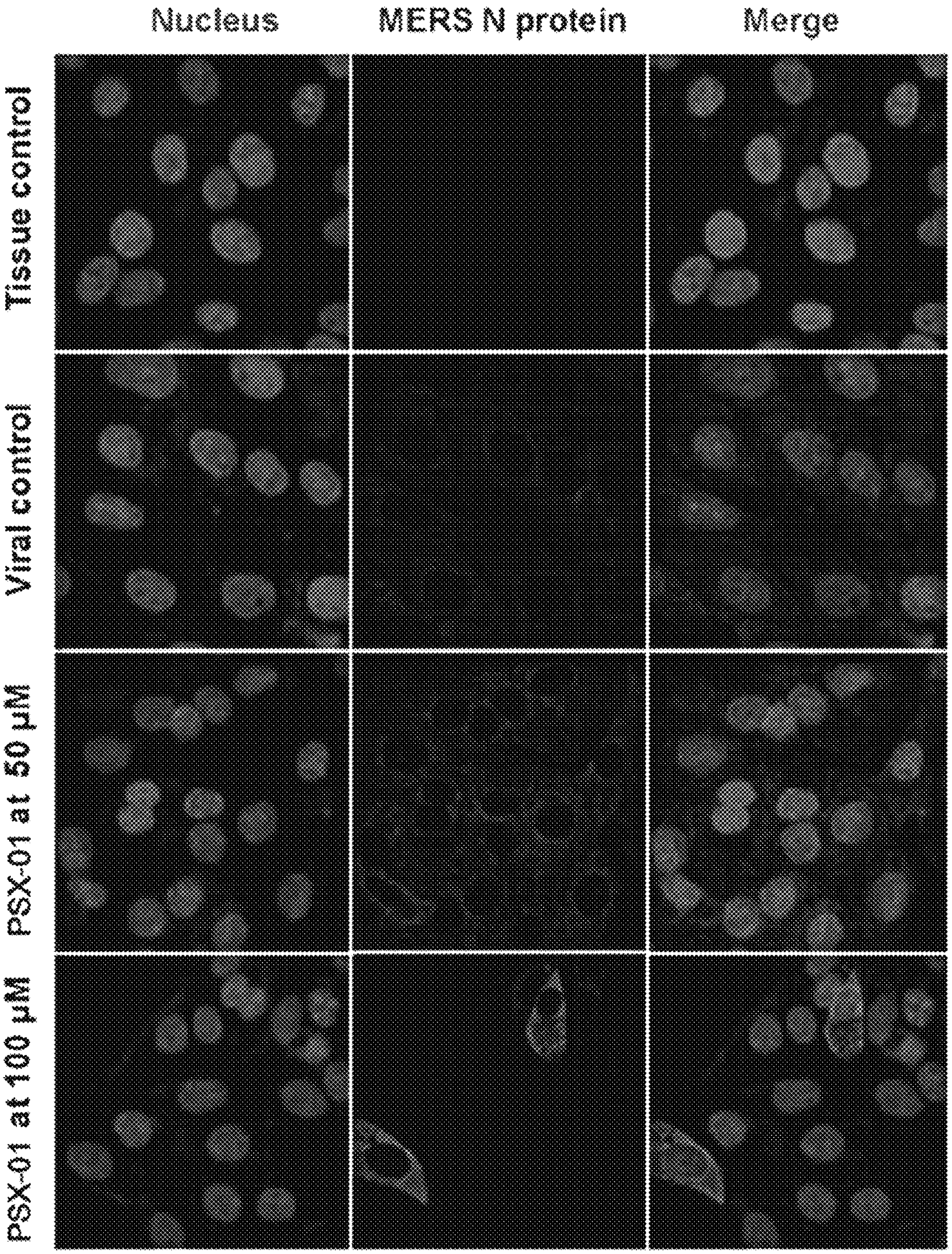

MERS-CoV N protein distribution and expression in the infected cells with or without PSX-01 treatment were then examined to confirm the SAXS findings. Immunofluorescence microscopy (FIG. 4C) showed condensation of the intracellular N protein fluorescence signal in infected Vero E6 cells treated with 50 μM PSX-01. Thus, PSX-01 may induce intracellular N protein aggregation. At 100 μM, PSX-01 suppressed N protein expression in most cells. However, a few presented with intense N protein signals. PSX-01 may have restrained the MERS-CoV N proteins inside the infected cells that promoted the formation of new virions that could not be released. In this way, the adjacent cells could not be infected with MERS-CoV. The data, therefore, suggested that PSX-01 may inhibit MERS-CoV by inducing abnormal aggregation of the N protein inside the cells. This finding is consistent with the results of the structure-based assays.

Example 5: Crystal Structure of MERS-CoV N-NTD Complexed with Chosen Compounds Crystals of MERS-CoV N-NTD in complex with compounds P1, P2, and PSX-01 were obtained by co-crystallization or ligand-soaking. With the exception of P2, the complex structures of N-NTD with P1 and PSX-01 were solved at resolutions of 3.09 and 2.77 Å, respectively. The overall structures of the complexes resembled that of apo-MERS-CoV. Both complexes revealed well-defined unbiased densities in the dimer interface and permitted detailed analysis of the interactions between the compounds and MERS-CoV N-NTD.

Figure 5:
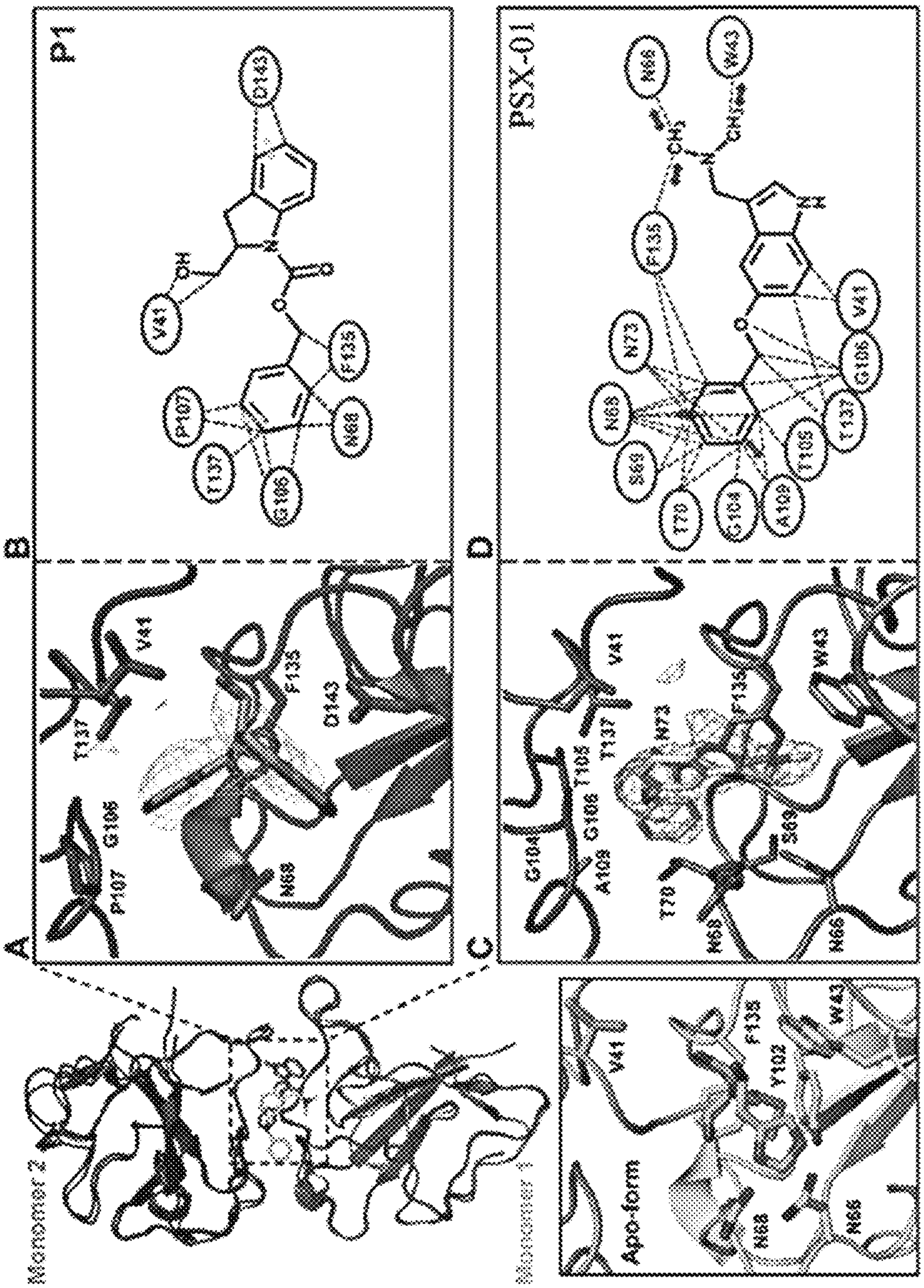
FIG. 5 is a schematic diagram showing the structures of MERS-CoV N-NTD complexed with chosen compounds. The structures were solved using HCoV-OC43 N-NTD (PDB: 4J3K) as the search model. Left panel: (Upper) structural superimposition of the MERS-CoV N-NTD:P1 complex (monomers 1 and 2) and the MERS-CoV N-NTD: PSX-01 complex (monomers 1 and 2) with compounds depicted as stick structures. (Lower) Interactions involving vector-fusion residues in the non-native dimer of the apoprotein shown for comparison with (A) and (C). Color is the same as in FIG. 1A. Right panel: detailed interactions among MERS-CoV N-NTD and P1 (A, B) and PSX-01 (C, D). Different Fo-Fc maps were contoured at around 2.5 σ. (A) Detailed stereoview of interactions at the P1-binding site. The color of each monomer is the same as in the left panel. Residues constructing the P1-binding pocket are labeled and showed as sticks. (B) Schematic plot of P1 bound to MERS-CoV N-NTD. Hydrophobic contacts between P1 and each monomer are displayed as dashed lines. Nonbonding interactions are indicated by arrows. (C) Detailed stereoview of interactions at the PSX-01-binding site. The color of each monomer is the same as in the left panel. Residues belonging to the PSX-01-binding pocket are labeled and shown as sticks. (D) Schematic plot of PSX-01 bound to MERS-CoV N-NTD. Hydrophobic contacts between PSX-01 and each monomer are displayed as dashed lines. Nonbonding interactions are indicated by arrows.

As shown in FIG. 5, the interactions between the N protein and each compound were calculated with the Discovery Studio Client (v19.1.0.18287). Most interactions were hydrophobic contacts. In the P1 complex, N68, F135, and D143 on monomer 1 and V41, G106, P107, and T137 on monomer 2 packed against P1 to create a dimer. In addition, two nonbonding interactions were detected between P1 and the monomers. There was a π-anion interaction between the benzene ring of the P1 indoline moiety and D143 of monomer 1. There was also a π-donor hydrogen bond between the other P1 benzene ring and the T137 side chain of monomer 2.

Relative to P1, PSX-01 bound more deeply into the dimer interface and interacted with a larger number of residues on both N-NTD monomers. The amino acid composition of this binding region was W43, N66, N68, S69, T70, N73, and F135 on monomer 1 and V41, G104, T105, G106, A109, and T137 on monomer 2. These residues along with PSX-01 generated a massive hydrophobic driving force, allowing the proteins and ligands to pack against each other and stabilize the dimeric conformation of the N protein. Several nonbonding interactions were also observed at the PSX-01-binding site. These included the interaction between the PSX-01 benzene ring and N68 of monomer 1 and A109 of monomer 2 via π-lone pair and π-alkyl interactions. The dimethylaminomethyl moiety of PSX-01 was a major source of nonbonding interactions. Three π-cation interactions were formed between this moiety and the aromatic groups of W43 and F135 in monomer 1. This moiety also formed a π-lone pair interaction with N66 and a π-sigma interaction with W43 of monomer 1.

The structural analyses explained the comparatively stronger binding of PSX-01 to N-NTD and corroborated the thermal stabilization effects and antiviral activities of the compounds.

Example 6: The Anti-Coronavirus Effect of PSX-01

In this example, in addition to MERS-CoV, SARS-CoV2 (i.e., the virus of COVID-19, provided by Professor Kylene Kehn-Hall, National Center for Biodefense and Infectious Diseases, School of Systems Biology, George Mason University, United States), mouse hepatitis virus (MHV), and porcine epidemic diarrhea virus (PEDV) (both were provided from Professor Hung-Yi Wu, Graduate Institute of Veterinary Pathobiology, College of Veterinary Medicine, National Chung Hsing University, Taiwan) were also used as targets for evaluating the antiviral effect of the PSX-01 compound.

For the evaluation, the cytotoxic concentration ($CC_{50}$) and effective concentration ($EC_{50}$) for PSX-01 were first measured by using Vero E6 cells infected with MERS-CoV and SARS-CoV2. In this example, Vero E6 cells were infected with MERS-CoV or SARS-CoV2 with multiplicity of infection (M.O.I.)=0.1 and treated with lead compounds for 48 h.

Figure 6:
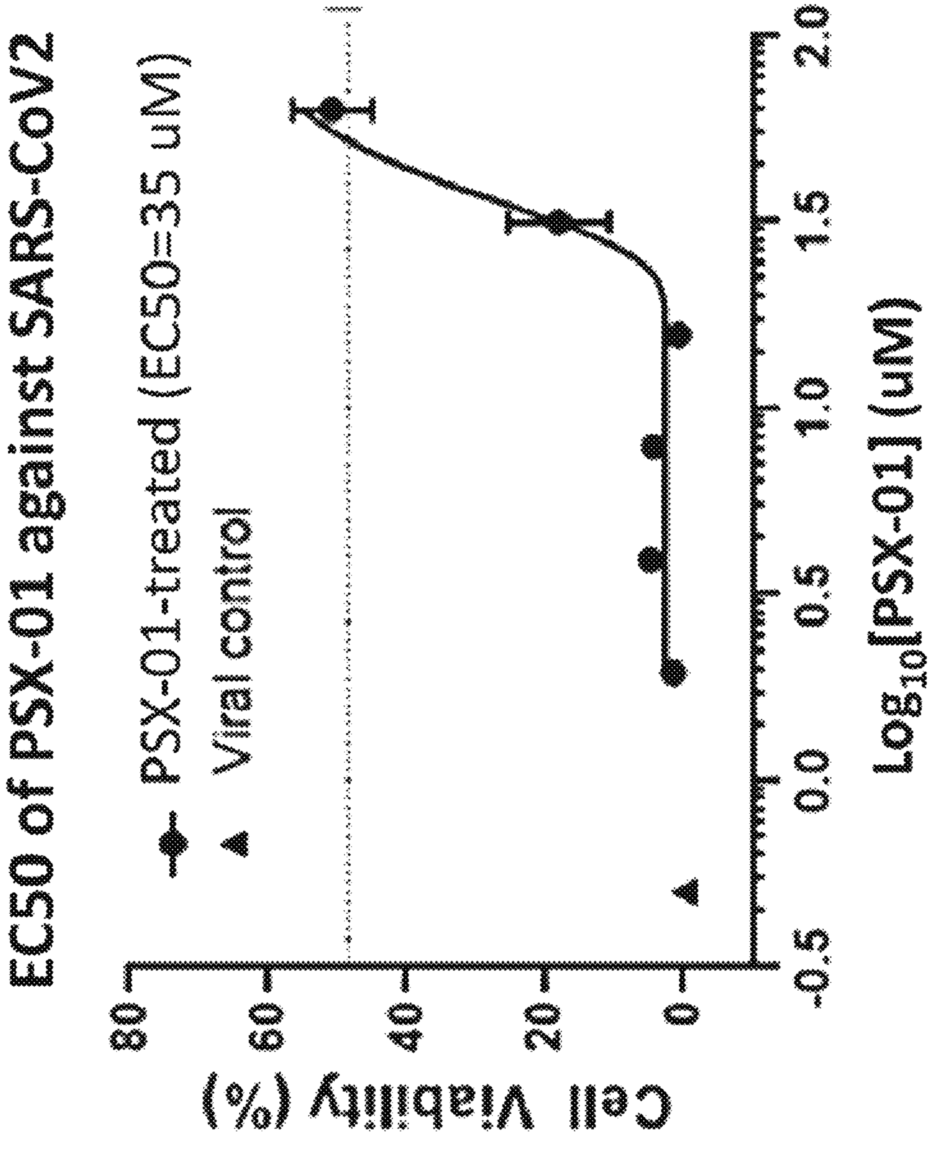
FIG. 6 shows the cell viability of Vero E6 cells infected with SARS-CoV2 (i.e., the virus of COVID-19) and treated with or without PSX-01. $EC_{50}$: effective concentration.

The results were shown in FIG. 6 and Table 5 below. The therapeutic index (TI) showed that PSX-01 had a favorable score among the lead compounds tested, and PSX-01 is a candidate inhibitor against MERS-CoV or SARS-CoV2.

TABLE 5

$CC_{50}$, $EC_{50}$ and therapeutic indexes of PSX-01

| PSX-01 (μM) | MERS-CoV | SARS-CoV2 |
|---|---|---|
| $CC_{50}$ | 805.32 | 800 |
| $EC_{50}$ | 32.1 | 35 |
| TI* | 25.1 | 23 |

*TI = $CC_{50}/EC_{50}$

Further, the antiviral activity of PSX-01 against MHV, PEDV, and MERS-CoV were evaluated. In this example, Vero E6 cells were seeded in 12-well plates and incubated overnight before the assays. Vero E6 cells were infected with MHV, PEDV, or MERS-CoV at indicated hours post infection (h.p.i.). At 24 h.p.i. (MHV), 30 h.p.i. (PEDV), or 48 h.p.i. (MERS-CoV), the cytopathic effect of the cells was examined with microscope. The images were also obtained with digital camera.

Figure 7A:
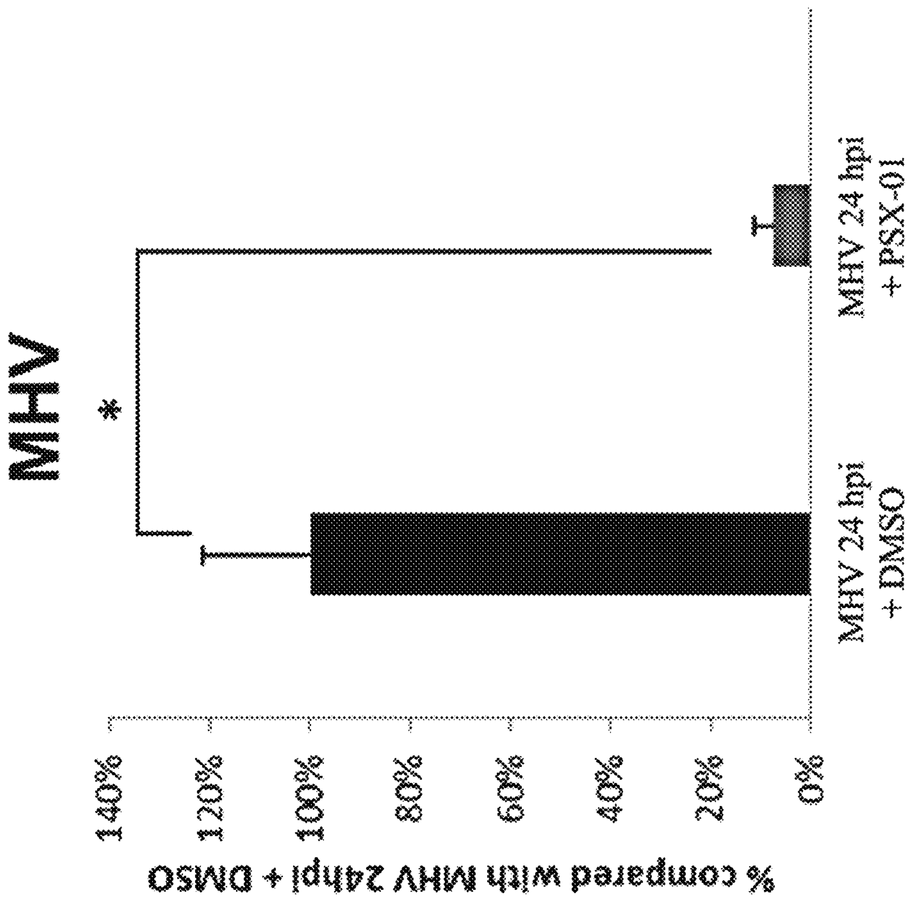
FIGS. 7A to 7C show the cytopathic effects for PSX-01 using Vero E6 cells infected with MHV, PEDV, or MERS-CoV.
Figure 7B:
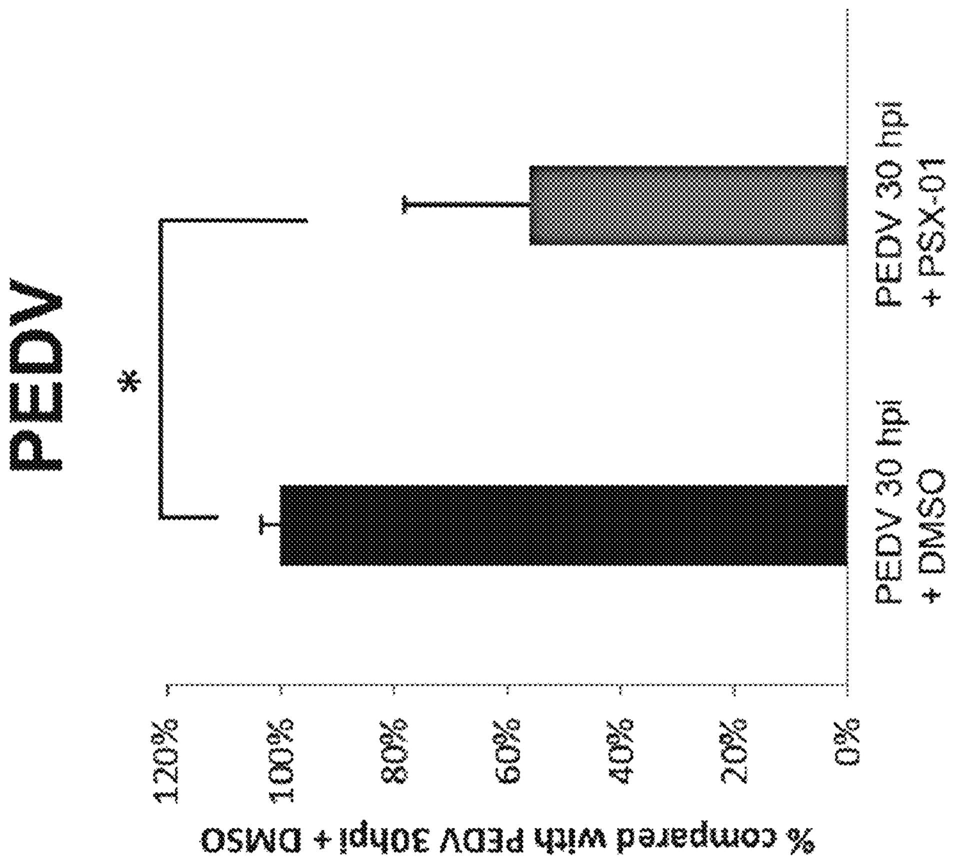
Figure 7C:
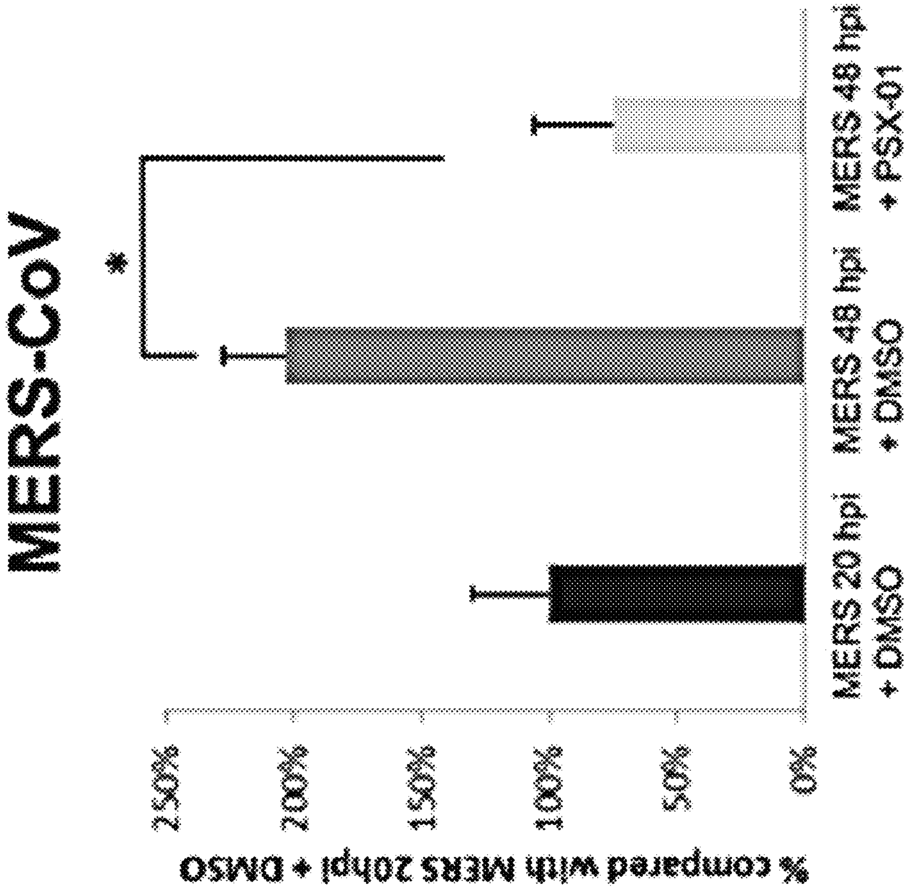

As shown in FIGS. 7A to 7C, PSX-01 may significantly reduce the cytopathic effect resulting from infections of MHV, PEDV, and MERS-CoV, indicating that PSX-01 is a candidate inhibitor against various CoVs.

Figure 8:
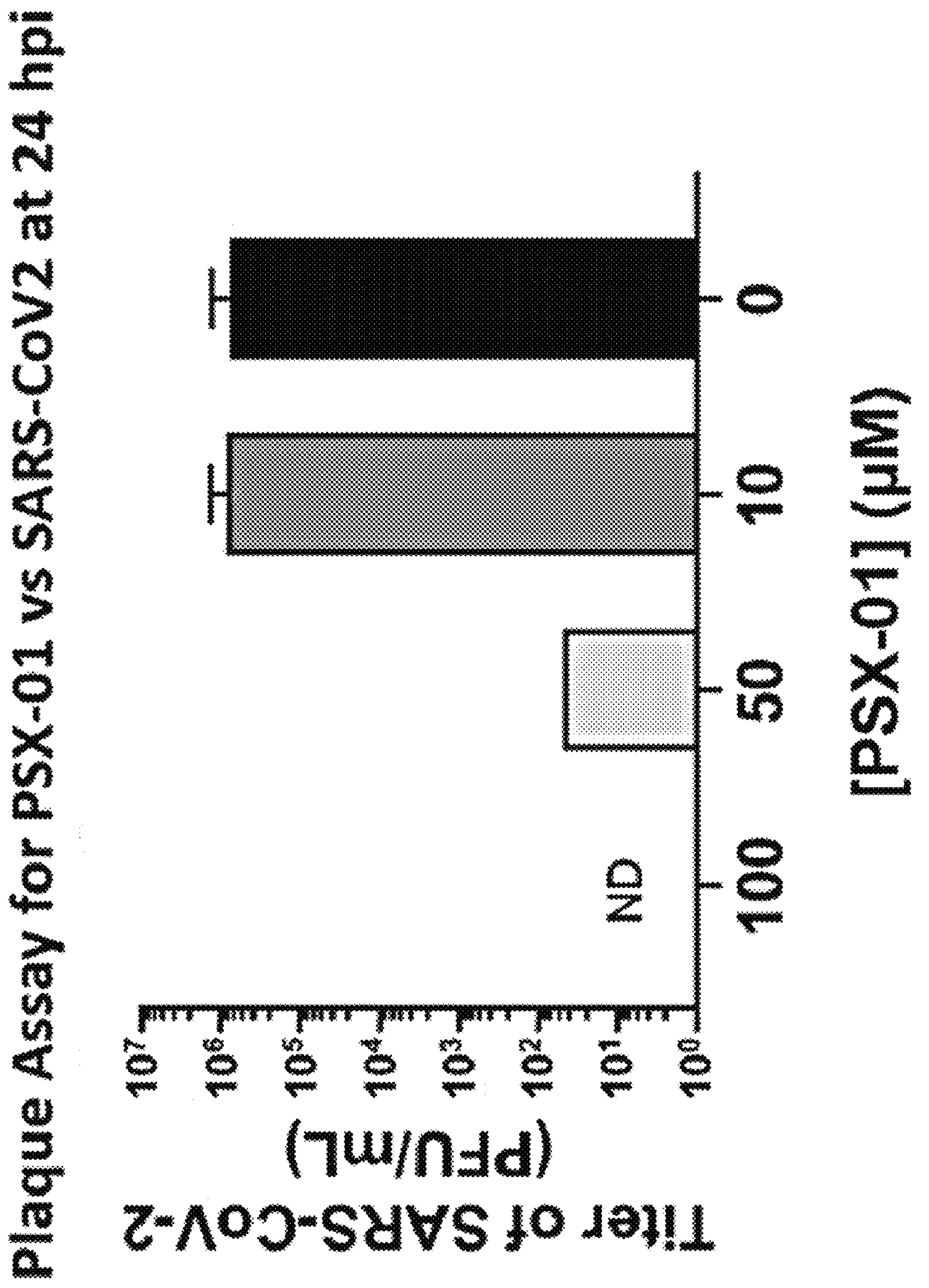
FIG. 8 shows that the viral titers of SARS-CoV2 measured by plaque assay decrease after PSX-01 treatment for 24 h.

Also, the effect of PSX-01 incubation on viral titers of SARS-CoV2 was assessed by plaque assays on Vero E6 cells. As shown in FIG. 8, at 50 μM or at 100 μM, PSX-01 affected the viral titer after 24 h. Further, in comparison with the result of plaque assay for MERS-CoV shown in FIG. 4A, it may be observed that PSX-01 has a superior antiviral effect against SARS-CoV2. These results proved the capacity of PSX-01 as an antiviral compound against coronaviruses, e.g., against SARS-CoV2.

Example 7: Toxicity Assessment of PSX-01

Three-week-old Balb/c mice were used in this example. The mice were divided into 4 groups, i.e., (1) Control group, (2) PSX-01 (10 mM) group, (3) virus ($10^4$ pfu) group, and (4) virus ($10^4$ pfu)+PSX-01 (10 mM) group.

For the drug treatment, the mice of each group were intraperitoneally injected with PSX-01 or saline. After 4 hours, the mice of the groups (2) to (4) were intraperitoneally injected with the MHV solution (500 μL) having a concentration of $10^4$ pfu. As to the Control group, the mice were injected with a culture solution (500 μL). The mice were observed and inspected after injection. The appearance was scored according to the following criteria: (A) rough fur at head and back received a score of 1; (B) rough fur at head, back and ventral received a score of 2; (C) mental depression (arched back) received a score of 3; and (D) death received a score of 4. The appearance was observed every 6 hours, and the body weight was measured every 12 hours.

The animals were sacrificed after 7 days, and their livers were collected, weighed, and photographed for record. A portion of each liver specimens was stored at −80° C., and the remaining liver specimens were soaked in 10% neutral formalin for hematoxylin and eosin stain (H&E stain).

Figure 9A:
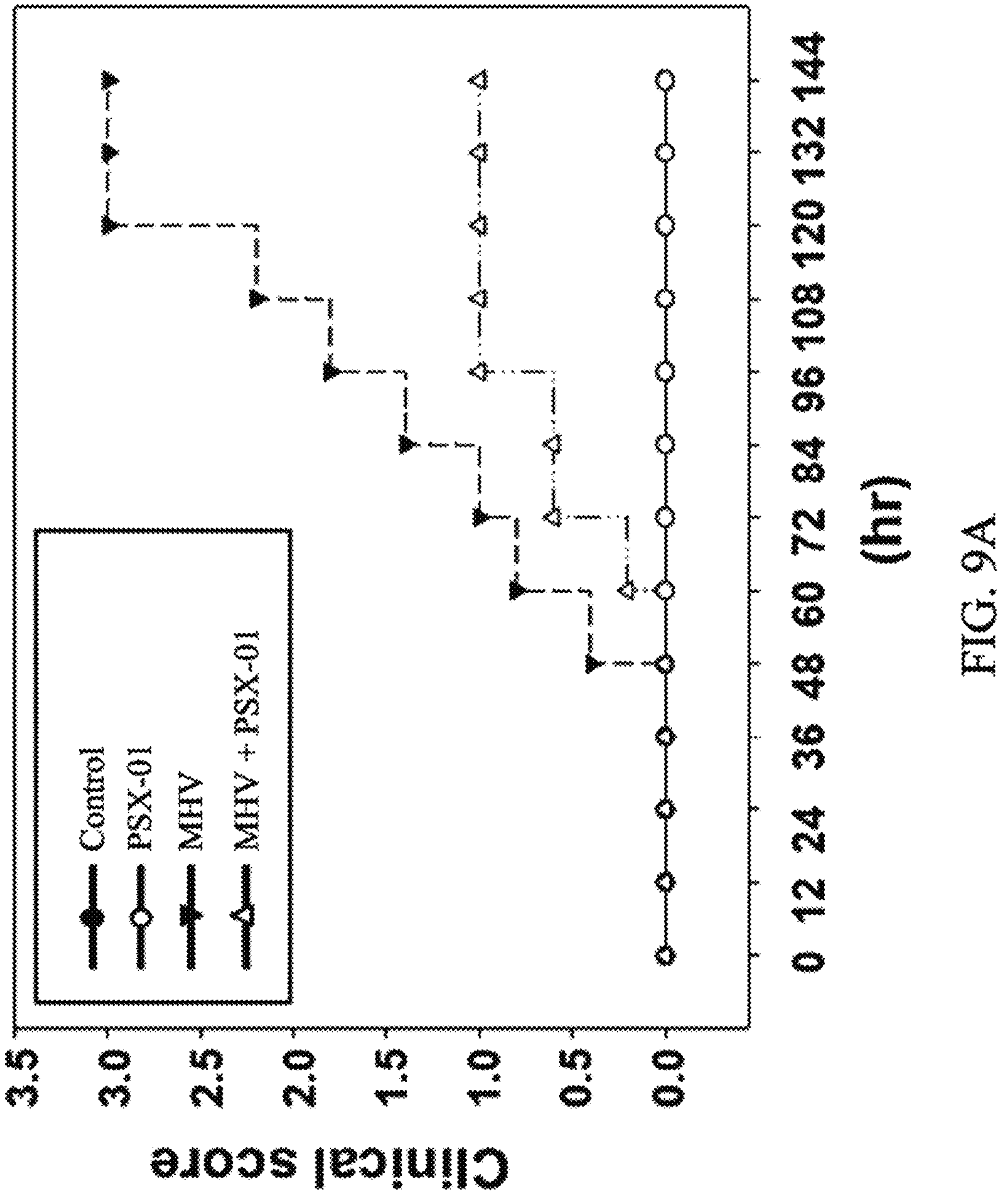
FIGS. 9A to 9C show the clinical score, the body weight, and the liver histology of MHV-infected mice treated with or without PSX-01.
Figure 9B:
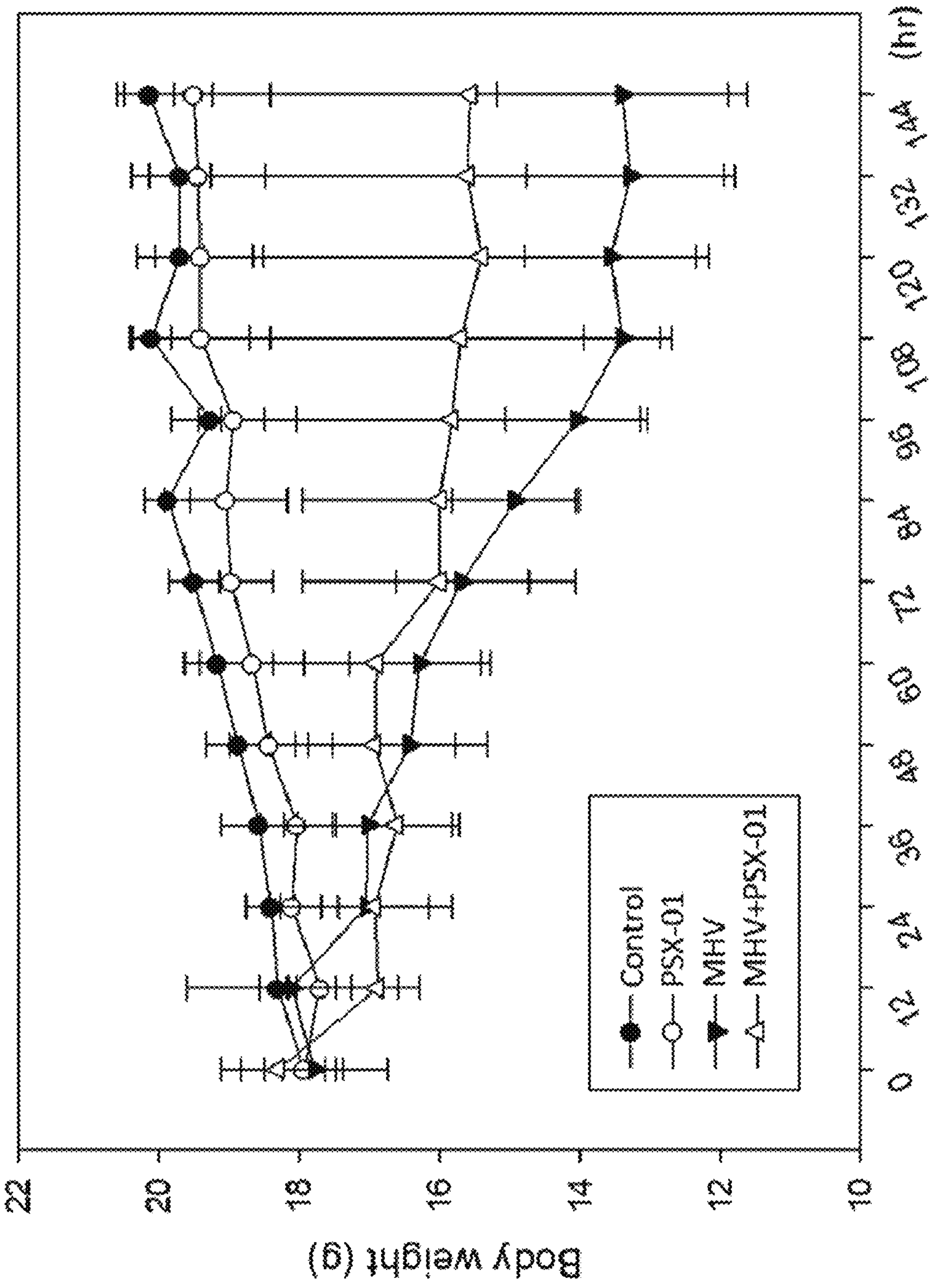
Figure 9C:
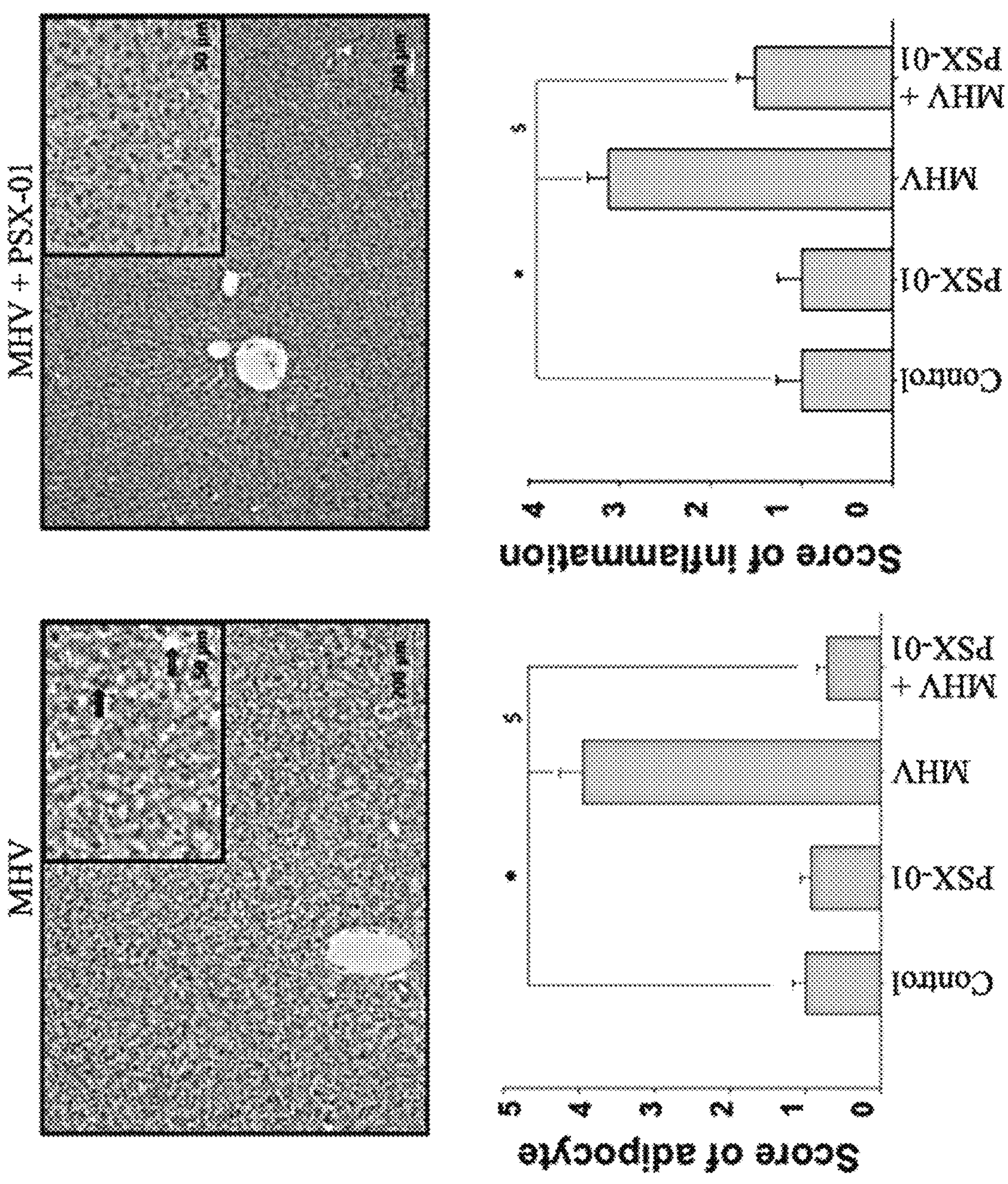

Referring to FIGS. 9A and 9B, the results demonstrated that PSX-01 may prevent the appearance change caused by MHV, and would not result in weight loss. Further, FIG. 9C showed the results of the histology of liver from MHV infection mice and PSX-01-treated mice compared by H&E staining, indicating that PSX-01 may rescue the increases of adipocytes and inflammation induced by MHV infection in liver.

From the above, these results indicate the indole derivatives provided in the present application are useful for coronavirus treatments with high tolerable dose.

While some of the embodiments of the present disclosure have been described in detail above, it is, however, possible for those of ordinary skill in the art to make various modifications and changes to the embodiments shown without substantially departing from the teaching and advantages of the present disclosure. Such modifications and changes are encompassed in the scope of the present disclosure as set forth in the appended claims.

REFERENCE

[1] Wang, Y S.; Chang, C. K.; Hou, M. H. Crystallographic analysis of the N-terminal domain of middle east respiratory syndrome coronavirus nucleocapsid protein. Acta Crystallogr., Sect. F: Struct. Biol. Commun. 2015, 71, 977-980.

[2] Adams, P.; Grosse-Kunstleve, R. W.; Hung, L.-W.; Ioerger, T. R.; McCoy, A. J.; Moriarty, N.; Read, R. J.; Sacchettini, J. C.; Sauter, N.; Terwilliger, T. PHENIX: building new software for automated crystallographic structure determination. Acta Crystallogr., Sect. D: Biol. Crystallogr. 2002, 58, 1948-1954.

[3] Emsley, P.; Cowtan, K. Coot: model-building tools for molecular graphics. Acta Crystallogr., Sect. D: Biol. Crystallogr. 2004, 60, 2126-2132.

[4] Chang, C. K.; Chen, C. M.; Chiang, M. H.; Hsu, Y. L.; Huang, T. H., Transient oligomerization of the SARS-CoV N protein—implication for virus ribonucleoprotein packaging. PloS One 2013, 8 (5), e65045.

[5] Gui, M.; Liu, X.; Guo, D.; Zhang, Z.; Yin, C.-C.; Chen, Y.; Xiang, Y., Electron microscopy studies of the coronavirus ribonucleoprotein complex. Protein & Cell 2017, 8 (3), 219-224.

What is claimed is:

1. A method for screening a compound having an inhibitory activity against a coronavirus in a host cell, comprising identifying a compound modulating a non-native protein-protein interaction in coronaviral nucleocapsid (N) proteins, wherein the compound is represented by formula (II) below:

(II)

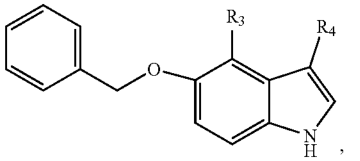

and wherein $R_3$ is H or a substituted alkoxy, and $R_4$ is H or a substituted moiety selected from the group consisting of alkyl, aralkyl, heteroaralkyl, and aminoalkyl, with the proviso that $R_3$ and $R_4$ are not H at the same time.

2. The method according to claim 1, wherein the coronavirus is severe acute respiratory syndrome coronavirus (SARS-CoV), middle east respiratory syndrome coronavirus (MERS-CoV), SARS-CoV2, mouse hepatitis virus (MHV), or porcine epidemic diarrhea virus (PEDV).

3. The method according to claim 1, wherein the non-native protein-protein interaction is a dimerization of N-terminal domains of the N proteins (N-NTDs), and the compound stabilizes the dimerization.

4. The method according to claim 3, wherein the identifying is detecting a hydrophobic contact formed between the compound and a hydrophobic pocket of a dimeric interface of the N-NTDs.

5. The method according to claim 4, wherein the hydrophobic contact is formed between the compound and at least one of V41, W43, and F135 in the hydrophobic pocket.

6. The method according to claim 4, wherein the hydrophobic contact is formed between the compound and at least one of V41, W43, N66, N68, N73 and F135 in the hydrophobic pocket.

7. The method according to claim 4, wherein the hydrophobic contact is formed between the compound and at least one of V41, W43, N66, N68, S69, T70, N73, G104, T105, G106, A109, F135 and T137 in the hydrophobic pocket.

* * * * *

SEQUENCE LISTING

```
<160> NUMBER OF SEQ ID NOS: 15

<210> SEQ ID NO 1
<211> LENGTH: 140
<212> TYPE: PRT
<213> ORGANISM: Middle East respiratory syndrome-related coronavirus

<400> SEQUENCE: 1

Met Ala Ser Pro Ala Ala Pro Arg Ala Val Ser Phe Ala Asp Asn Asn
1               5                   10                  15

Asp Ile Thr Asn Thr Asn Leu Ser Arg Gly Arg Gly Arg Asn Pro Lys
            20                  25                  30

Pro Arg Ala Ala Pro Asn Asn Thr Val Ser Trp Tyr Thr Gly Leu Thr
        35                  40                  45

Gln His Gly Lys Val Pro Leu Thr Phe Pro Pro Gly Gln Gly Val Pro
    50                  55                  60

Leu Asn Ala Asn Ser Thr Pro Ala Gln Asn Ala Gly Tyr Trp Arg Arg
65                  70                  75                  80

Gln Asp Arg Lys Ile Asn Thr Gly Asn Gly Ile Lys Gln Leu Ala Pro
                85                  90                  95

Arg Trp Tyr Phe Tyr Tyr Thr Gly Thr Gly Pro Glu Ala Ala Leu Pro
```

-continued

```
            100                 105                 110

Phe Arg Ala Val Lys Asp Gly Ile Val Trp Val His Glu Asp Gly Ala
        115                 120                 125

Thr Asp Ala Pro Ser Thr Phe Gly Thr Arg Asn Pro
    130                 135                 140


<210> SEQ ID NO 2
<211> LENGTH: 166
<212> TYPE: PRT
<213> ORGANISM: Human coronavirus

<400> SEQUENCE: 2

Met Ser Phe Thr Pro Gly Lys Gln Ser Ser Ser Arg Ala Ser Ser Gly
1               5                   10                  15

Asn Arg Ser Gly Asn Gly Ile Leu Lys Trp Ala Asp Gln Ser Asp Gln
            20                  25                  30

Phe Arg Asn Val Gln Thr Arg Gly Arg Arg Ala Gln Pro Lys Gln Thr
        35                  40                  45

Ser Thr Ser Gln Gln Pro Leu Gly Gly Asn Val Val Pro Tyr Tyr Ser
    50                  55                  60

Trp Phe Ser Gly Ile Thr Gln Phe Gln Lys Gly Lys Glu Phe Glu Phe
65                  70                  75                  80

Ala Glu Gly Gln Gly Val Pro Ile Ala Pro Gly Val Pro Ala Thr Glu
                85                  90                  95

Ala Lys Gly Tyr Trp Tyr Arg His Asn Arg Arg Ser Phe Lys Thr Ala
            100                 105                 110

Asp Gly Asn Gln Arg Gln Leu Leu Pro Arg Trp Tyr Phe Tyr Tyr Leu
        115                 120                 125

Gly Thr Gly Pro His Ala Lys Asp Gln Tyr Gly Thr Asp Ile Asp Gly
    130                 135                 140

Val Phe Trp Val Ala Ser Asn Gln Ala Asp Val Asn Thr Pro Ala Asp
145                 150                 155                 160

Ile Val Asp Arg Asp Pro
                165


<210> SEQ ID NO 3
<211> LENGTH: 169
<212> TYPE: PRT
<213> ORGANISM: Murine hepatitis virus

<400> SEQUENCE: 3

Met Ser Phe Val Pro Gly Gln Glu Asn Ala Gly Ser Arg Ser Ser Ser
1               5                   10                  15

Gly Ser Arg Ser Gly Asn Gly Ile Leu Lys Lys Thr Thr Trp Ala Asp
            20                  25                  30

Gln Thr Glu Arg Ala Gly Asn Asn Gly Asn Arg Gly Arg Arg Asn Gln
        35                  40                  45

Pro Lys Gln Thr Ala Thr Thr Gln Pro Asn Ser Gly Ser Val Val Pro
    50                  55                  60

His Tyr Ser Trp Phe Ser Gly Ile Thr Gln Phe Gln Lys Gly Lys Glu
65                  70                  75                  80

Phe Gln Phe Val Gln Gly Gln Gly Val Pro Ile Ala Asn Gly Ile Pro
                85                  90                  95

Ala Ser Glu Gln Lys Gly Tyr Trp Tyr Arg His Asn Arg Arg Ser Phe
            100                 105                 110

Lys Thr Pro Asp Gly Gln Gln Lys Gln Leu Leu Pro Arg Trp Tyr Phe
```

```
        115                 120                 125

Tyr Tyr Leu Gly Thr Gly Pro His Ala Gly Ala Glu Tyr Gly Asp Asp
    130                 135                 140

Ile Glu Gly Val Val Trp Val Ala Ser Gln Gln Ala Asp Thr Lys Thr
145                 150                 155                 160

Thr Ala Asp Ile Val Glu Arg Asp Pro
                165


<210> SEQ ID NO 4
<211> LENGTH: 152
<212> TYPE: PRT
<213> ORGANISM: Severe acute respiratory syndrome coronavirus

<400> SEQUENCE: 4

Met Ser Asp Asn Gly Pro Gln Ser Asn Gln Arg Ser Ala Pro Arg Ile
1               5                   10                  15

Thr Phe Gly Glu Pro Thr Asp Ser Thr Asp Asn Asn Gln Asn Gly Gly
            20                  25                  30

Arg Asn Gly Ala Arg Pro Lys Gln Arg Arg Pro Gln Gly Leu Pro Asn
        35                  40                  45

Asn Thr Ala Ser Trp Phe Thr Ala Leu Thr Gln His Gly Lys Glu Glu
    50                  55                  60

Leu Arg Phe Pro Arg Gly Gln Gly Val Pro Ile Asn Thr Asn Ser Gly
65                  70                  75                  80

Pro Asp Asp Gln Ile Gly Tyr Tyr Arg Arg Ala Thr Arg Arg Val Arg
                85                  90                  95

Gly Gly Asp Gly Lys Met Lys Glu Leu Ser Pro Arg Trp Tyr Phe Tyr
            100                 105                 110

Tyr Leu Gly Thr Gly Pro Glu Ala Ser Leu Pro Tyr Gly Ala Asn Lys
        115                 120                 125

Glu Gly Ile Val Trp Val Ala Thr Glu Gly Ala Leu Asn Thr Pro Lys
    130                 135                 140

Asp His Ile Gly Thr Arg Asn Pro
145                 150


<210> SEQ ID NO 5
<211> LENGTH: 164
<212> TYPE: PRT
<213> ORGANISM: Bat coronavirus

<400> SEQUENCE: 5

Met Ser Gly Arg Asn Lys Pro Arg Pro Gly Ser Gln Ser Pro Lys Val
1               5                   10                  15

Thr Phe Lys Gln Glu Ser Asp Gly Ser Asp Ser Glu Ser Glu Arg Arg
            20                  25                  30

Asn Gly Asn Arg Asn Gly Ala Arg Pro Lys Asn Asn Asn Gly Arg Gly
        35                  40                  45

Ala Gly Ser Lys Pro Glu Lys Pro Lys Ala Ala Pro Pro Gln Asn Val
    50                  55                  60

Ser Trp Tyr Ala Pro Leu Val Gln Thr Gly Lys Asn Asp Leu Arg Phe
65                  70                  75                  80

Pro Arg Gly Gln Gly Val Pro Ile Ser Gln Gly Ile Asp Asp Ile Tyr
                85                  90                  95

Asn His Gly Tyr Trp Val Arg Thr Gln Arg Asn Phe Gln Lys Gly Gly
            100                 105                 110

Lys Gln Val Ala Ala Asn Pro Arg Trp Tyr Phe Tyr Tyr Thr Gly Thr
```

-continued 115 120 125

Gly Arg Tyr Ala Asp Leu Arg Tyr Gly Ser Lys Asn Pro Asp Ile Ile
130 135 140

Trp Val Gly Ala Glu Gly Ala Asn Ile Asn Arg Val Gly Asp Ile Gly
145 150 155 160

Thr Arg Asn Pro

<210> SEQ ID NO 6
<211> LENGTH: 39
<212> TYPE: DNA
<213> ORGANISM: Artificial Sequence
<220> FEATURE:
<223> OTHER INFORMATION: N39A-Forward

<400> SEQUENCE: 6
ccgcgcggca gccatatggc gaccgtgagc tggtatacc 39

<210> SEQ ID NO 7
<211> LENGTH: 39
<212> TYPE: DNA
<213> ORGANISM: Artificial Sequence
<220> FEATURE:
<223> OTHER INFORMATION: N39A-Reverse

<400> SEQUENCE: 7
ggtataccag ctcacggtcg ccatatggct gccgcgcgg 39

<210> SEQ ID NO 8
<211> LENGTH: 39
<212> TYPE: DNA
<213> ORGANISM: Artificial Sequence
<220> FEATURE:
<223> OTHER INFORMATION: N39G-Forward

<400> SEQUENCE: 8
ccgcgcggca gccatatggg caccgtgagc tggtatacc 39

<210> SEQ ID NO 9
<211> LENGTH: 39
<212> TYPE: DNA
<213> ORGANISM: Artificial Sequence
<220> FEATURE:
<223> OTHER INFORMATION: N39G-Reverse

<400> SEQUENCE: 9
ggtataccag ctcacggtgc ccatatggct gccgcgcgg 39

<210> SEQ ID NO 10
<211> LENGTH: 39
<212> TYPE: DNA
<213> ORGANISM: Artificial Sequence
<220> FEATURE:
<223> OTHER INFORMATION: W43A-Forward

<400> SEQUENCE: 10
catatgaaca ccgtgagcgc gtataccggc ctgacccag 39

<210> SEQ ID NO 11
<211> LENGTH: 39
<212> TYPE: DNA
<213> ORGANISM: Artificial Sequence
<220> FEATURE:
<223> OTHER INFORMATION: W43A-Reverse

<400> SEQUENCE: 11

-continued

```
ctgggtcagg ccggtatacg cgctcacggt gttcatatg                        39


<210> SEQ ID NO 12
<211> LENGTH: 19
<212> TYPE: DNA
<213> ORGANISM: Artificial Sequence
<220> FEATURE:
<223> OTHER INFORMATION: GAPDH-F

<400> SEQUENCE: 12

gaaggtgaag gtcggagtc                                              19


<210> SEQ ID NO 13
<211> LENGTH: 20
<212> TYPE: DNA
<213> ORGANISM: Artificial Sequence
<220> FEATURE:
<223> OTHER INFORMATION: GAPDH-R

<400> SEQUENCE: 13

gaagatggtg atgggatttc                                             20


<210> SEQ ID NO 14
<211> LENGTH: 21
<212> TYPE: DNA
<213> ORGANISM: Artificial Sequence
<220> FEATURE:
<223> OTHER INFORMATION: MERS-CoV-F

<400> SEQUENCE: 14

ccactactcc catttcgtca g                                           21


<210> SEQ ID NO 15
<211> LENGTH: 26
<212> TYPE: DNA
<213> ORGANISM: Artificial Sequence
<220> FEATURE:
<223> OTHER INFORMATION: MERS-CoV-R

<400> SEQUENCE: 15

cagtatgtgt agtgcgcata taagca                                      26
```